United States Patent [19]

Kobayashi et al.

[11] Patent Number: 5,245,671
[45] Date of Patent: Sep. 14, 1993

[54] APPARATUS FOR INSPECTING PRINTED CIRCUIT BOARDS AND THE LIKE, AND METHOD OF OPERATING SAME

[75] Inventors: Shigeki Kobayashi; Yasuaki Tanimura; Teruhisa Yotsuya, all of Kyoto, Japan

[73] Assignee: Omron Corporation, Kyoto, Japan

[21] Appl. No.: 601,722

[22] PCT Filed: May 2, 1989

[86] PCT No.: PCT/JP89/00470

§ 371 Date: Oct. 26, 1990

§ 102(e) Date: Oct. 26, 1990

[87] PCT Pub. No.: WO89/11093

PCT Pub. Date: Nov. 16, 1989

[30] Foreign Application Priority Data

| Sep. 5, 1988 | [JP] | Japan | 63-112054 |
| Sep. 9, 1988 | [JP] | Japan | 63-226767 |
| Sep. 9, 1988 | [JP] | Japan | 63-226768 |
| Sep. 12, 1988 | [JP] | Japan | 63-227963 |
| Sep. 12, 1988 | [JP] | Japan | 63-227964 |
| Sep. 14, 1988 | [JP] | Japan | 63-230738 |

[51] Int. Cl.$^5$ ............................................. G06K 9/00
[52] U.S. Cl. ..................................... 382/8; 382/1; 382/17; 356/418
[58] Field of Search .............. 382/1, 8, 17; 356/402, 356/418; 250/226; 364/526

[56] References Cited

U.S. PATENT DOCUMENTS

| 4,249,827 | 2/1981 | DiMatteo et al. | 382/17 |
| 4,677,473 | 6/1987 | Okamota et al. | 356/101 |
| 4,688,939 | 8/1987 | Ray | 356/237 |
| 4,727,498 | 2/1988 | Ehrlich et al. | 356/402 |
| 4,730,930 | 3/1988 | Thoreson et al. | 356/418 |
| 4,952,972 | 8/1990 | Someya | 356/418 |
| 4,971,437 | 11/1990 | van Gijzel | 358/418 |

FOREIGN PATENT DOCUMENTS

| 231941 | 8/1987 | European Pat. Off. |
| 236738 | 9/1987 | European Pat. Off. |
| 263473 | 4/1988 | European Pat. Off. |
| 385474 | 9/1990 | European Pat. Off. |
| 59-153108 | 9/1984 | Japan |

OTHER PUBLICATIONS

IBM Technical Disclosure Bulletin, vol. 30, No. 4, Sep. 1987, pp. 1647–1649.
IBM Technical Disclosure Bulletin, vol. 29, No. 6, Nov. 1986, pp. 2702–2703.
AT&T Technical Journal, vol. 67, No. 2, Apr. 1988, pp. 47–60.

*Primary Examiner*—Jose L. Couso
*Attorney, Agent, or Firm*—Fish & Richardson

[57] ABSTRACT

Disclosed is an inspection apparatus for a printed circuit board or the like for inspecting the shape of the soldered portion of a part mounted on the printed circuit board, and for judging whether the soldered portion is acceptable or not. In order to illuminate a printed circuit board undergoing inspection, there are provided three types of ring shaped light-emitting elements, which respectively generate red light, green light and blue light, arranged at positions to project this light, at angles of incidence that differ from one another, toward the surface of a body to be inspected. Light rays of the three primary colors emitted by these light-emitting elements have light-emission energy distributions with respect to wavelength that provide white light when these light rays are mixed, and the quantities of light emitted are adjusted in such a manner that white light is obtained. As a result, three-colored light images regarding the surface of the object under inspection can be detected, and it is possible to detect also peripheral information (part number, polarity, color code, various marks, etc.) essential in solder inspections.

The present invention discloses also a method of teaching with regard to the mounted position of a part, the type thereof, and a feature quantity of the mounted state, a method of setting an inspection zone on a printed circuit board, and a method of displaying the results of inspection, etc. These methods are performed prior to inspection of the printed circuit board in the inspecting apparatus.

5 Claims, 18 Drawing Sheets

Fig. 5
| | SOLDER ACCEPTABLE | PART MISSING | SOLDER UNACCEPTABLE |
|---|---|---|---|
| SECTIONAL VIEW | 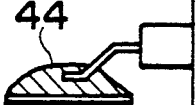 | 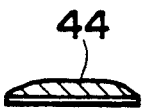 | 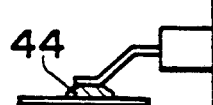 |
| IMAGED PATTERN | 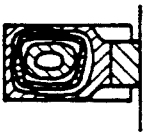 |  | 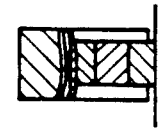 |
| RED PATTERN |  | 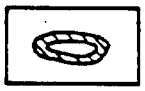 |  |
| GREEN PATTERN |  | 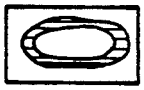 |  |
| BLUE PATTERN |  |  |  |

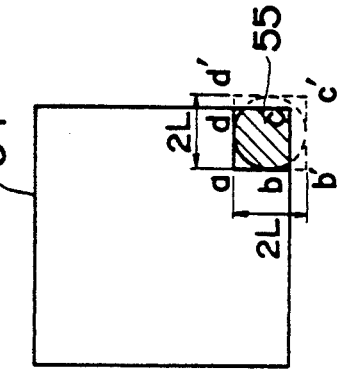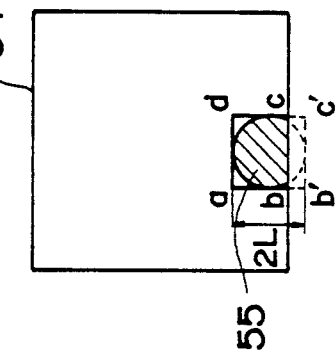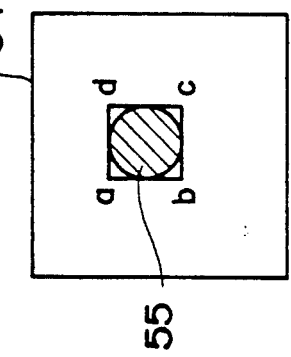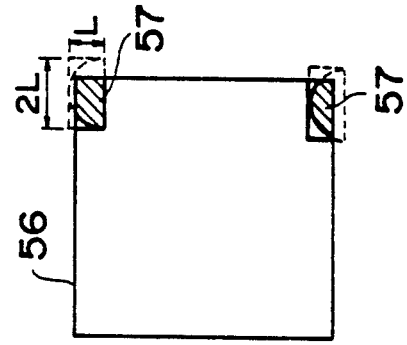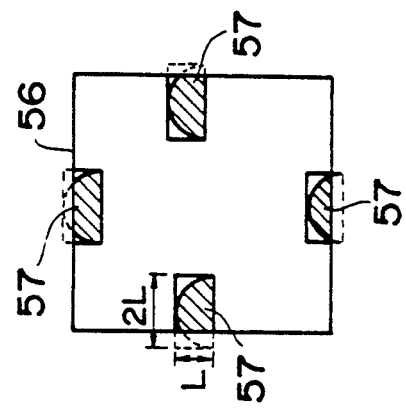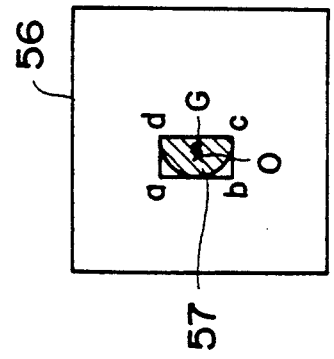

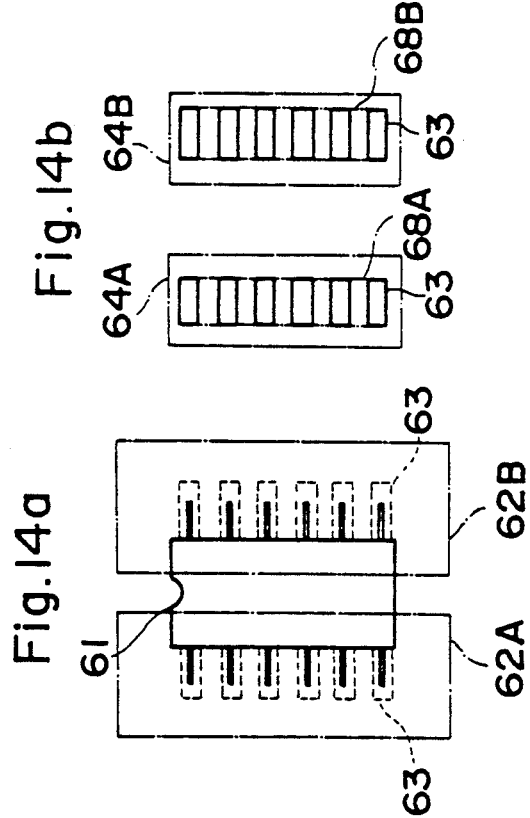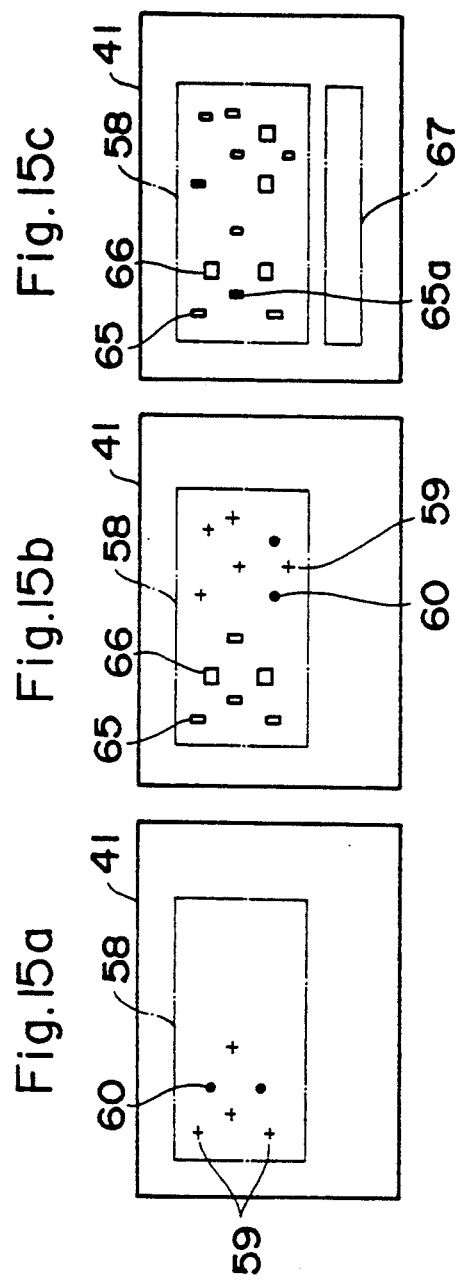

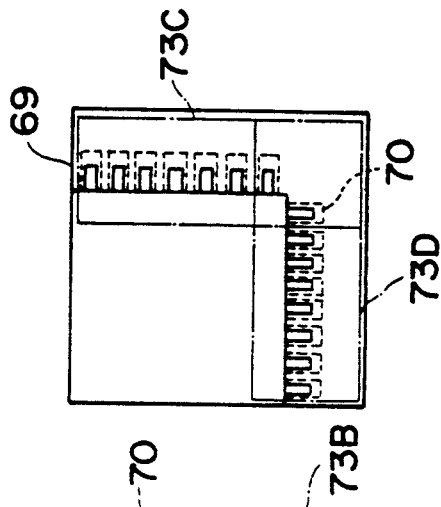
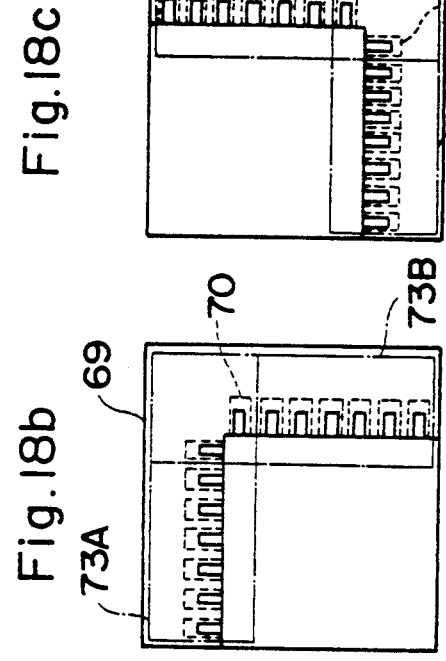
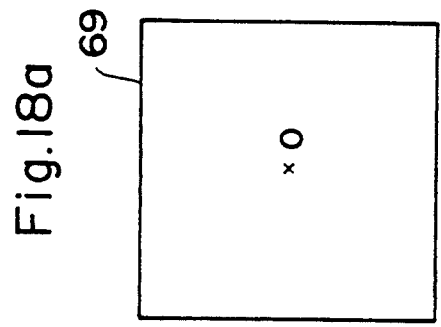
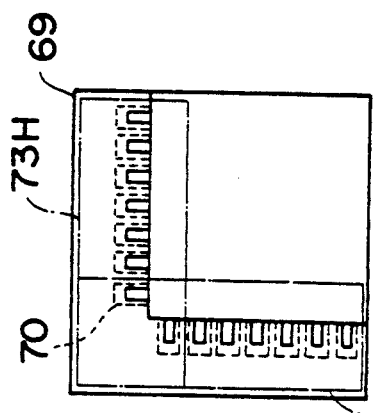
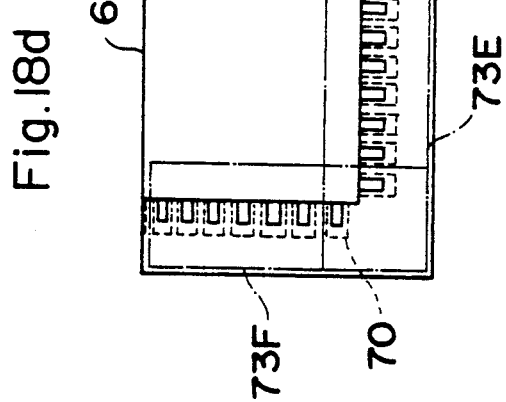

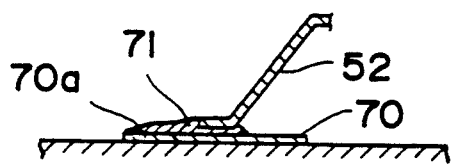
Fig.21a
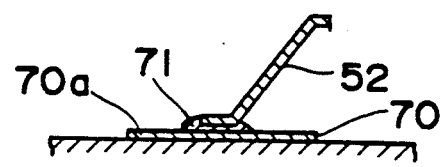
Fig.21b
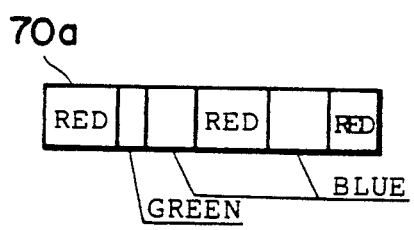
Fig.22a
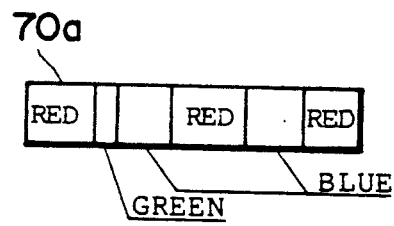
Fig.22b
Fig.23
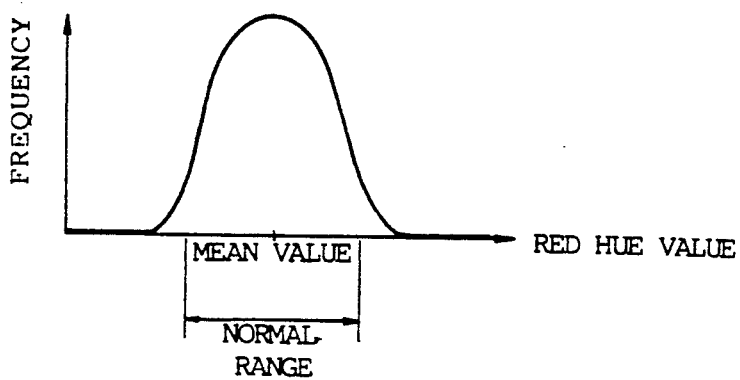

APPARATUS FOR INSPECTING PRINTED CIRCUIT BOARDS AND THE LIKE, AND METHOD OF OPERATING SAME

DESCRIPTION

1. Technical Field

This invention relates to an apparatus for inspecting a printed circuit board (hereinafter referred to as a "PC board") or the like, and to a method of operating the apparatus. More particularly, the invention relates to an apparatus which inspects the properties of a curved surface and is applied in detecting the orientation of curved-surface elements of a curved-surface body comprising a set of a number of curved-surface elements the surfaces whereof are oriented in different directions; an apparatus which inspects the properties of a curved surface and is ideal for inspecting the shape of a soldered portion of a part mounted on a PC board; a PC board inspecting apparatus for extracting hue patterns in the three primary colors from an original image obtained by imaging a part mounted on a PC board, comparing the extracted results with taught data and judging the acceptability of the mounted state of the part, such as the soldered state; a teaching method for teaching, prior to inspection of the PC board, the mounted position of a part, the class of the mounted part and feature quantities of the mounted state of the part in the abovementioned inspecting apparatus; a method of setting an inspection zone for setting, prior to inspection of the PC board, a mounted-part inspection zone in the abovementioned inspecting apparatus; a method of displaying inspection results for displaying the results of part inspection on the screen of a display unit in the abovementioned inspecting apparatus; and a display method in a PC board inspecting apparatus ideal for verifying the acceptability of the extracted state of hue patterns.

2. Background Art

The shape of the surface of a soldered region of a part mounted on a PC board can be mentioned as a typical example of a curved-surface body having a multiple-oriented surface. Conventionally, such a soldered region is inspected visually, and the acceptability of the soldered state, namely the absence or presence of solder, the amount of solder and its solubility, short circuits and improper conduction are judged based on this visual inspection.

With this method using such visual inspection, however, the occurrence of inspection error cannot be avoided, judgment differs widely depending upon the individual performing the inspection, and there are limits upon inspection processing capability.

In recent years, a variety of automatic inspection apparatus capable of performing an inspection of this kind automatically have been proposed.

The shape of the surface of a soldered region is a cubic shape of three dimensions, and the ability to detect three-dimensional shape information is essential in order to inspect such a shape.

FIG. 1 illustrates an example of an automatic inspection apparatus capable of detecting three-dimensional shape information. The apparatus irradiates a soldered region on a PC board 2 with slit light 1. A reflected-light image of an optical cutting-plane line 3, which is produced on the surface of the PC board 2 inclusive of the soldered region by irradiation with the slit light 1, is picked up by an image pickup device 4, and the three-dimensional shape of the soldered portion is detected by investigating the imaged pattern.

With this inspection method, however, all that is obtained is shape information indicative of the portion irradiated with the slit light 1, and it is difficult to ascertain the three-dimensional shape of other portions. Moreover, the surface of the soldered region is such that the orientation thereof is not uniform with respect to the surface direction of the PC board. Consequently, at least four combinations of light source and image pickup device 4 are necessary. For this reason, the apparatus is complicated and a highly precise assembling operation is required. A problem is that this invites higher cost.

Accordingly, in order to solve this problem, a method is available in which the surface of a curved-surface body undergoing inspection is irradiated with light from a plurality of directions having different angles of incidence, each reflected-light image from the surface of the curved-surface body is imaged, and the orientation of the curved-surface elements possessed by the curved-surface body is detected from the respective imaged patterns. This method belongs to the class of "active sensing methods", which is one of the methods of detecting three-dimensional image information. Specifically, this method takes note of the fact that when light flux having a uniform pattern is projected upon the object undergoing inspection, the pattern of the reflected light flux obtained from the object undergoes deformation in accordance with the three-dimensional shape of the object. The method is such that the shape of the object under inspection is estimated from the deformed pattern.

FIG. 2 is a diagram for describing the principle of this method and shows the positional relationship between a detecting system, which comprises a light projecting device 5 and an image pickup device 6, and a curved-surface body 7, which is the object undergoing inspection.

When light flux 8 is projected toward the surface of the curved-surface body (e.g., a soldered region) 7 from the projecting device 5 disposed as a certain position, reflected light flux 9 impinges upon and is detected by the image pickup device 6 placed immediately overhead. When this is done, it is detected that a curved-surface element of the portion of the curved-surface body 7 irradiated with the light flux 8 is oriented at an angle $\theta$ with respect to a horizontal reference plane 10 ($\theta$ is the angle of incidence). Accordingly, if light is projected upon the surface of the curved-surface body 7 using a plurality of projecting devices having different angles of incidence in a case where the surface property of the curved-surface body 7 is such that the curved surface comprises a number of curved-surface elements oriented in different directions, as is the case with a soldered surface, a group of curved-surface elements corresponding to respective ones of these angles of incidence can be detected, whereby it is possible to detect how each curved-surface element of the surface of the curved-surface body 7 is oriented, namely what the surface property of the soldered region is.

If the projecting device 5 is one which projects a light flux 8 having a width $\Delta\theta$, reflected light flux 9 having a width corresponding to this width will be detected by the image pickup device 6. In other words, in this case curved-surface elements having the width $\Delta\theta$ for an angle can be detected.

Further, if the projecting device 5 includes ring shaped light-emitting elements 11, 12 and 13 arranged horizontally with respect to the reference plane 10, as shown in FIG. 3, the distance between the projecting device 5 and the curved-surface body 7 will be constant regardless of the rotational angle of the curved-surface body 7 with respect to an axis perpendicular to the reference plane 10, and the orientations of the curved-surface elements in the direction of the angle of rotation thereof will be cancelled out. As a result, only the angle of inclination of the curved-surface body 7 with respect to the reference plane 10 will be detected.

If the projecting device 5 is constituted by the plurality of ring-shaped light-emitting elements 11, 12 and 13 having different angles of incidence relative to the curved-surface body 7, as shown in FIG. 3, curved-surface elements having orientations corresponding to the angles of incidence of light fluxes 14, 15 and 16 from the light-emitting elements can be detected in detail, as set forth above.

Assume that the three ring-shaped light-emitting elements 11, 12 and 13 of radii $r_m$ (m=1, 2, 3) are disposed horizontally at positions having heights $h_m$ (m = 1, 2, 3) from the reference surface 10, and that the angles of incidence of the light fluxes 14, 15, 16 from these light-emitting elements 11, 12, 13 relative to the curved-surface body 7 are $\theta_m$ (m=1, 2, 3). Under these assumptions, curved surface elements whose angles of inclination at the curved-surface body 7 respectively are $\theta_m$ can be detected by the image pickup device 6. In comparison with total optical paths from the light-emitting elements 11, 12, 13 to the image pickup device 6 via the surface of the curved-surface body 7, the sizes of the curved-surface elements are sufficiently small. Therefore, the angles of incidence, namely the angles of inclination of the curved-surface elements to be detected, can be determined in accordance with the following equation:

$$cos\theta_m = h_m/(h_m^2 + r_m^2)^{\frac{1}{2}} \qquad (1)$$

A method employing sources of white light as the light-emitting elements 11, 12, 13 has been proposed as a method of inspecting the external appearance of a soldered region on the basis of the foregoing principle [Japanese Patent Application Laid-Open (KOKAI) No. 61-293657)]. In this method of inspection, the light-emitting elements 11, 12, 13 are lit and extinguished at respectively different timings in order distinguish among the reflected-light images produced by the three light-emitting elements 11, 12, 13 having different angles of incidence with respect to the soldered surface.

However, with this method of controlling the lighting of the light-emitting elements, there is need of a memory for the purpose of storing each image obtained at each of the different projection timings, an arithmetic unit for processing these images as an image of an identical visual field, and a firing device for lighting each light-emitting element instantaneously. This entails great technical complexity and the method involves problems in terms of cost and reliability.

Accordingly, in an effort to solve all of these problems encountered in such a time-sharing system, a method has been proposed for use in an apparatus which inspects linear bodies such as wires [Japanese Patent Application Laid-Open (KOKAI) No. 62-127617)]. According to this method, light sources for the three primary colors of red, green and blue are used as the three light-emitting elements having different angles of incidence with respect to the object undergoing inspection. Reflected-light images in the colors red, green and blue from the object are imaged at the same timing by a hue-sensing-type image pickup device such as a color television camera, and the images are detected upon undergoing color separation.

When this method is applied to an automatic inspection apparatus for inspecting soldered regions, it is theoretically possible to detect the curved-surface property of a soldered region in a short period of time. However, since this apparatus is not contrived to detect peripheral information essential for automatic inspection of parts mounted on a PC board, such as information relating to each region on the PC board (e.g., part number, polarity, color code, etc) and circuit-board pattern information (various marks on the circuit board), it is extremely difficult to put the apparatus to practical use as is.

When an apparatus for inspecting a PC board is used, a teaching operation is required in which various data relating to a PC board (referred to as a "reference PC board") having prescribed parts correctly mounted at predetermined positions are entered from a keyboard before the PC board is inspected. This teaching operation is referred to simply as "teaching" and entails the teaching of data relating to the positions, types and inspection zones of parts mounted on a reference PC board, as well as data relating to feature quantities of the mounted state (e.g, the soldered state) within the inspection zone of each part.

With this teaching method using data entry by key, however, the amount of data to be keyed in is extremely large. As a consequence, an exorbitant amount of time and labor are necessary for the input operation, and operation is a great burden.

A teaching method for solving these problems has been proposed [Japanese Patent Application Laid-Open (KOKAI) No. 62-180251] and entails fabricating beforehand a positioning PC board (reference PC board) obtained by coloring the surface of a PC board with black paint and coloring mounted parts with white paint, and imaging the positioning PC board by a PC board inspecting apparatus, thereby teaching data (part position, etc.) serving as criteria for the purpose of inspecting the PC board.

However, according to this teaching method, not only does fabricating the positioning PC board require the painting operation, but the method is also uneconomical in that it is impossible to reutilize a painted PC board. In addition, part position cannot be taught correctly unless painting is performed in accurate fashion. Furthermore, according to this method, the teaching of items other than part position, such as the teaching of part type, cannot be performed with ease.

On the other hand, in a case where a feature quantities of soldered state are taught, the conventional practice is to prepare in advance a single reference PC board on which each part has been soldered normally, extract feature quantities of the soldered state of each part using this reference PC board, and thereafter provide the extracted quantities with a fixed width to decide the range of feature quantities that defines the normal soldered state.

However, there is absolutely no guarantee that a reference PC board prepared for teaching will be suitable for representing the correctly soldered state of each part. If such happens to be the case, a taught feature quantity will represent a biased value and not an average, and a situation will frequently occur in soldered state inspection in which mounting defects are overlooked or a soldered state within tolerance is judged to be defective under strict standards.

In order to obtain the feature quantities of the soldered state of a part in teaching or inspection, hue patterns composed of the three primary colors are extracted from an original image obtained by imaging the part mounted of the PC board. In order to realize proper inspection of a PC board, the inspection is premised on the fact that pattern extraction is performed accurately. To verify the acceptability of pattern extraction, conventional methods that have been proposed entail displaying obtained feature quantities in the form of numerical values on a display unit, or displaying an image, which is based on the results of extraction, at the position of the original image of the inspection zone obtained by imaging the part mounted on the PC board.

With the former of these methods, however, it is difficult to grasp the extracted state concretely since the display is based upon a numerical value. With the latter method, it is difficult to contrast the results of extraction with the original image since the original image vanishes from the display screen. A problem with both methods is that the acceptability of the extracted state cannot be verified with ease.

With regard to setting the inspection zone, conventionally the zone is fixedly determined by fixed coordinates. When a zone on the PC board which includes an inspection location is imaged during inspection, a zone of a portion of the image is extracted as an inspection zone using the fixed coordinates, and only the interior of the inspection zone extracted is processed. In order to shorten processing time, the inspection zone is set to be as small as possible. However, a problem encountered is that the location to be inspected will protrude to the exterior of the set inspection zone unless the precision of the driving mechanism for conveying and positioning the PC board, the PC board machining precision and the pattern printing precision, etc., are sufficiently high.

In order to solve this problem, the conventional approach is to set a reference pattern on the PC board, calculate the amount of offset between the position of this reference pattern obtained at the time of inspection and the position of a reference pattern obtained at the time of teaching, and then correct the position of the inspection zone.

According to this method, however, the fact that the reference pattern is required necessitates the printing of an extra pattern on all PC boards. Moreover, if an error occurs in the processing which detects the position of the reference pattern, this will have an influence upon the positions of all inspection zones.

In a case where a PC board undergoing inspection is imaged by the above-described PC board inspection apparatus and an inspection is performed to determine the acceptability of the mounted state of each part, namely whether parts are missing or the soldered state is acceptable, the results of inspection of each part are displayed on the screen of a CRT display unit and, when necessary, are printed out by means of a printer.

Conventional methods employed for displaying the results of inspection in a PC board inspection apparatus include a method in which the number of a defective part, the location of the defect and the particulars of the defect are displayed on a CRT display unit, and a method in which the mounted position of each part on the PC board is displayed and only those parts that are defective are displayed in a different color.

With the former method, however, it is difficult to achieve correspondence between the number of a defective part and the position of the part on the PC board. According to the latter method, the position of a defective part can be verified but the particulars of the defect are unclear. As a result, it is required that an inspector inspect the PC board and visually verify the particulars of the defect.

DISCLOSURE OF THE INVENTION

An object of the present invention is to provide an apparatus for inspecting the properties of a curved surface in which, by arranging it so that white light is obtained when irradiating light rays from a plurality of light-emitting elements constituting a projecting device are mixed, the properties of a curved surface of a curved-surface body such as a soldered region can be detected in a short period of time, and it becomes possible also to detect peripheral information essential for actual inspection.

Another object of the present invention is to provide a teaching method in a PC board inspecting apparatus in which, by using a label to teach the mounted position of a part and the type of the mounted part, fabrication of a reference PC board for teaching is facilitated and reuse of the PC board is made possible.

A further object of the present invention is to provide a teaching method in a PC board inspecting apparatus in which, by obtaining feature (characteristic) quantities of the mounted state of a part using a plurality of reference PC boards, it becomes possible to realize reliable and stable inspection of the mounted state of a part.

Still another object of the present invention is to provide an inspection zone setting method in a PC board inspecting apparatus in which, by processing an image obtained by imaging a PC board and setting an inspection zone of a mounted part, the inspection zone can be set stably and at high speed without requiring correction processing.

Yet another object of the present invention is to provide a method of displaying the results of inspection in a PC board inspecting apparatus in which, by adopting a system wherein the position of a defective (faulty) particulars of the defect (fault) are displayed simultaneously on one screen, it becomes possible to verify the position of the defective part and the particulars of the defect without requiring visual inspection of the PC board.

A further object of the present invention is to provide a display method in a PC board inspecting apparatus in which, by specially contriving a method of displaying the results of pattern extraction, the acceptability of the extracted state can be verified easily and accurately.

An apparatus for inspecting properties of a curved surface according to the present invention is characterized by comprising projecting means which includes three types of ring-shaped light-emitting elements, which are for generating red light, green light and blue light having light-emission energy distributions with respect to wavelength that provide white light upon being mixed, arranged at positions to project this light, at angles of incidence that differ from one another, toward a surface of a curved-surface body to be inspected, light-quantity adjusting means for adjusting the quantity of light of each light-emitting element in such a manner that white light is obtained when the light emitted from the light-emitting elements is mixed, image pickup means for imaging reflected-light images from the surface of the curved-surface body to obtain imaged patterns distinguished by hue, and processing means for detecting properties of a curved-surface element of the curved-surface body from the imaged patterns obtained from the image pickup means.

Red light, green light and blue light from the ring-shaped light-emitting elements irradiates the surface of the inspected curved-surface body at different angles of incidence. Since it is so arranged that the red, green and blue reflected-light images from the surface of the curved-surface body are detected simultaneously and distinguished by hue, the properties of the curved-surface body can be detected in a short time using the hue patterns obtained. Moreover, since it is set so that white light is obtained when the red, green and blue light rays emitted by the light-emitting elements are mixed, it is possible to detect essential peripheral information necessary in inspecting the solder of mounted parts, e.g., information (part number, polarity, color code, etc.) relating to each part on the PC board, as well as PC board pattern information (various marks and the like). In this way automation of soldered state inspection can be realized.

A teaching method of the invention for teaching the mounted position of a part and the type of the mounted part before a PC board is inspected to a PC board inspecting apparatus for inspecting the mounted state of a part mounted on the PC board includes supplying a PC board having labels affixed at the respective mounting positions of parts to the abovementioned PC board inspecting apparatus, and imaging the labels, whereby the mounted positions of the parts are taught by the positions at which the labels are affixed and the type of a part is taught by the color or shape of the label.

Before inspecting a PC board, a reference PC board is fabricated by affixing a label whose color or shape conforms to the type of a part at the mounting position of the part on the PC board. This reference PC board is supplied to the PC board inspecting apparatus and the labels are imaged, whereby the positions at which the labels are affixed as well as the shapes and colors of the labels are read. The positions at which the parts are mounted are taught from the positions at which the labels are affixed, and the type of a part is taught from the color or shape of the label for that part.

According to this teaching method, the reference PC board for teaching can be fabricated in simple fashion merely by affixing the labels. If the labels are peeled off, the PC board can be reutilized. This is economical. According to this teaching method, moreover, it is easy to teach part type and not just part position.

One more teaching method according to the present invention entails teaching of the feature quantities of the mounted state of a part before inspecting a PC board to a PC board inspecting apparatus for inspecting the mounted state of a part mounted on the PC board. According to this teaching method, a plurality of reference PC boards on which parts have been correctly mounted are successively supplied to the abovementioned PC board inspecting apparatus. The PC board inspecting apparatus is operated in such a manner that the plurality of reference PC boards supplied are imaged, the feature quantities of the mounted states of the parts are extracted from the resulting images, these feature quantities are processed statistically, and the calculated values are set as the feature quantities.

Thus, in accordance with the teaching method of the present invention, the feature quantities of the mounted states of the parts are extracted from the images of the plurality of reference PC boards, and the statistically processed values are taught to the PC board inspecting apparatus as feature quantities. Therefore, even if there is a statistical dispersion among the mounted states of a part from one PC board to another, the feature quantities are averaged by the statistical processing. As a result, incidents of overlooked improperly mounted parts or of normal parts being erroneously judged to be defective are reduced in inspecting the mounted states of parts, and PC boards can be inspected in reliable and stable fashion.

Furthermore, the present invention provides an inspection-zone setting method for setting an inspection zone of a mounted part prior to PC board inspection in a PC board inspection apparatus for inspecting a mounted part on a PC board. The method is characterized by imaging a supplied PC board to produce an image of the part mounting position, initially setting, with respect to the image, a processing zone which includes a land region on the PC board, extracting the land region by executing projection processing within the processing zone, and setting an inspection zone of the mounted part by enlarging, by a predetermined width, an area circumscribing the extracted land region.

In accordance with this inspection zone setting method of the present invention, a PC board is supplied to a PC board inspecting apparatus to image a part mounting position, and the resulting image is subjected to predetermined image processing to set an inspection zone of the mounted part, all before the PC board is inspected. Therefore, even if there is a deviation in the printed pattern on the PC board, an inspection zone which includes an inspection location can be set reliably and it is possible to set an inspection zone stably and at high speed. In addition, setting a reference pattern on a PC board and performing correction processing using such a reference pattern are unnecessary. Even if a deviation occurs in extraction of the inspection zone, there is no danger of this having an adverse influence upon the setting of all inspection zones.

A method of displaying the results of inspection according to the present invention in a PC board inspecting apparatus for imaging a plurality of parts mounted on a PC board, inspecting the mounted state of each part and displaying the results of inspecting each part on a screen of a display unit is characterized by displaying, in one area of the screen of the display unit, a mounted position of each part on the PC board in a predetermined color and a position of a part, judged to have mounting fault, in a color different from that of the positions of other parts, and simultaneously displaying, in another area, particulars of the defect of the defective part.

In accordance with this method of displaying the results of inspection of the present invention, the mounted position of each part on the PC board is displayed in a predetermined color on the screen of the display unit. With regard to a part judged to be defective, the position of this part is displayed in a color different from that of normal parts, and the particulars of the defect also are displayed simultaneously on the same screen. As a result, correspondence is readily established between a defective part and the position of this part on the PC board. Moreover, the particulars of the defect exhibited by the part can be grasped immediately, and the inspector need not inspect the PC board and perform a visual confirmation.

Further, the present invention provides one more display method. This method, in a PC board inspecting apparatus for extracting hue patterns in three primary colors from an original image obtained by imaging a mounted part on a PC board, comparing results of extraction with taught data and judging the acceptability of the mounted state of the part, is characterized by displaying, on a display screen of a display unit, the original image and an image, which is based on the results of extraction, adjacent the original image, and coloring the image based on the results of extraction using pseudo colors corresponding to the hue patterns.

An original image of an inspection zone obtained by imaging a mounted part on a PC board, and an image, based on the results of extraction, colored by respective ones of the pseudo colors corresponding to the hue patterns are displayed adjacent to each other on a display screen of a display unit. As a result, the inspector is capable of concretely grasping the extracted state and directly comparing the colors of both images, thus making it possible to readily verify the acceptability of the extracted state.

BRIEF DESCRIPTION OF THE DRAWINGS

FIG. 5 is a diagram showing the relationship between patterns and the acceptability of soldered states;

FIGS. 12a, 12b, 12c, 13a, and 13b and 13c are explanatory views showing the extracted images of labels and the circumscribing rectangles thereof on an image;

FIGS. 14a and 14b are explanatory views showing a method of setting inspection zones;

FIGS. 15a, 15b and 15c are diagrams showing display screens of a CRT display unit;

FIGS. 17a, 17b, 18a, 18b, 18c, 18d, 18e and 19 are diagrams showing methods of setting inspection zones with regard to a square part;

FIGS. 21a and 21b are sectional views showing the soldered states of a part;

FIGS. 22a and 22b are explanatory views showing imaged patterns of soldered regions;

FIG. 23 is a graph showing a data distribution of red hue values;

BEST MODE FOR CARRYING OUT THE INVENTION

Figure 1:
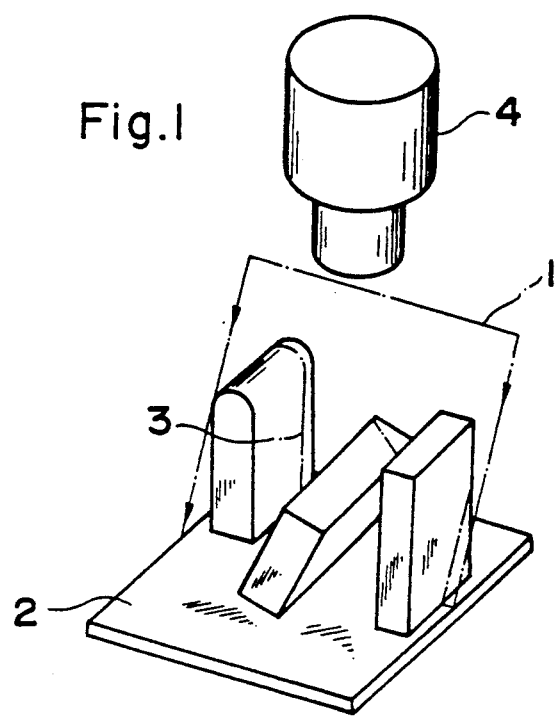
FIG. 1 is a perspective view for describing the inspection principle in an automatic inspecting apparatus according to the prior art.
Figure 2:
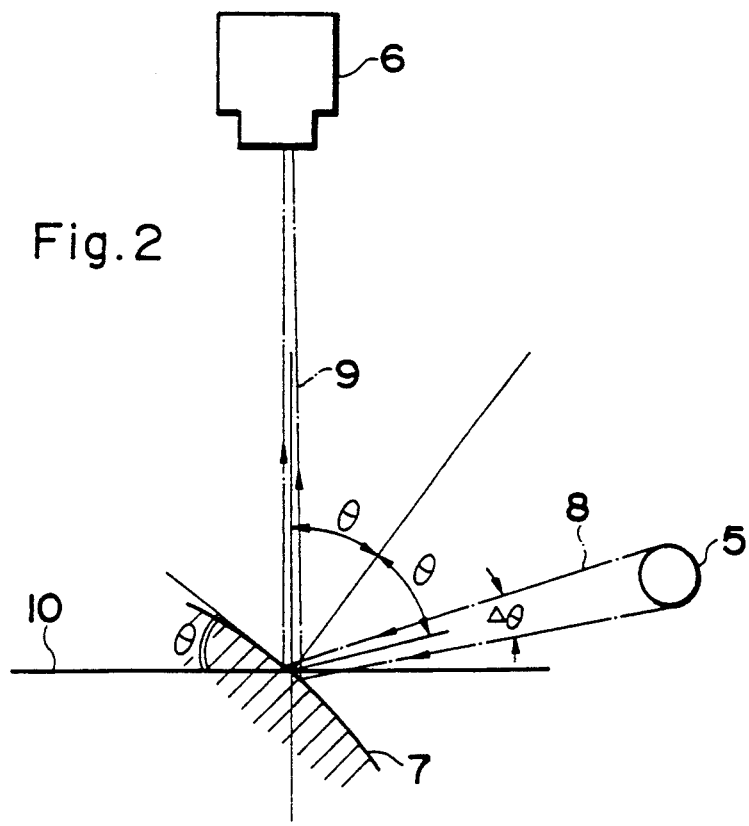
FIGS. 2 and 3 are explanatory views illustrating the inspection principle in an automatic inspecting apparatus.
Figure 3:
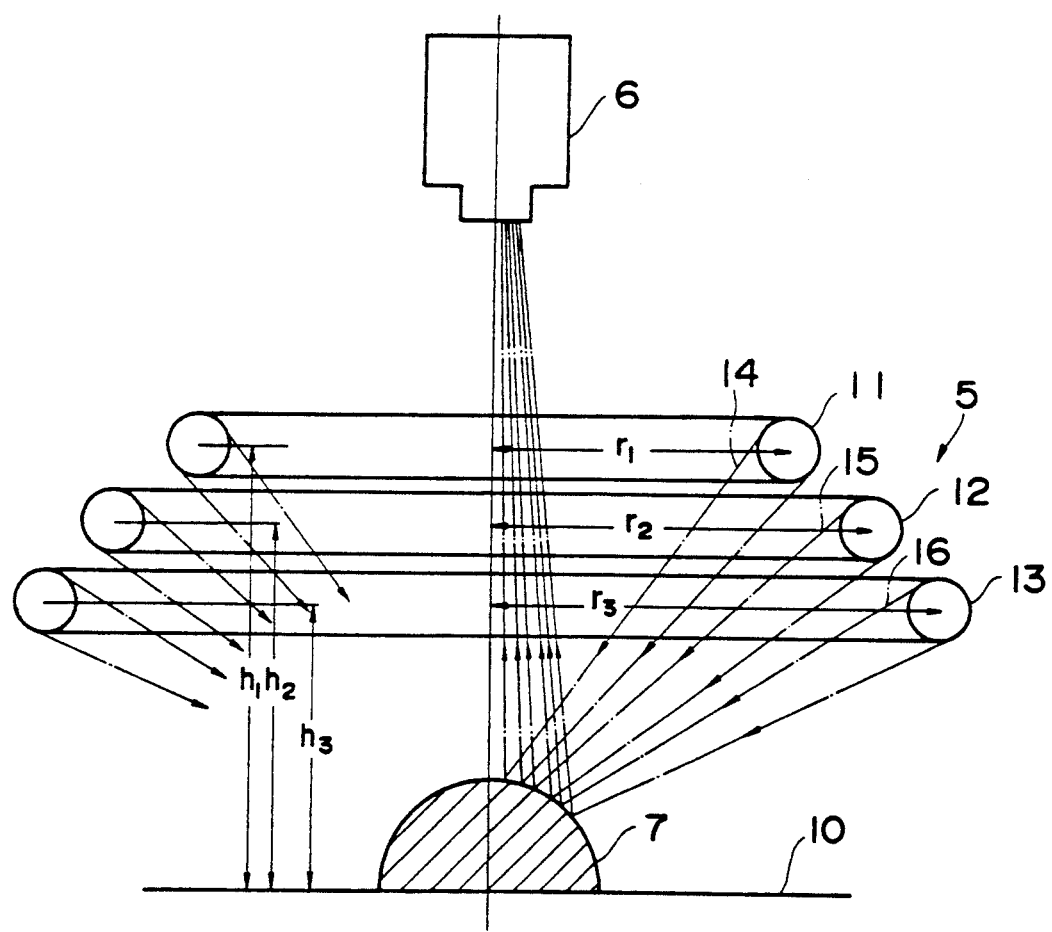
Figure 4:
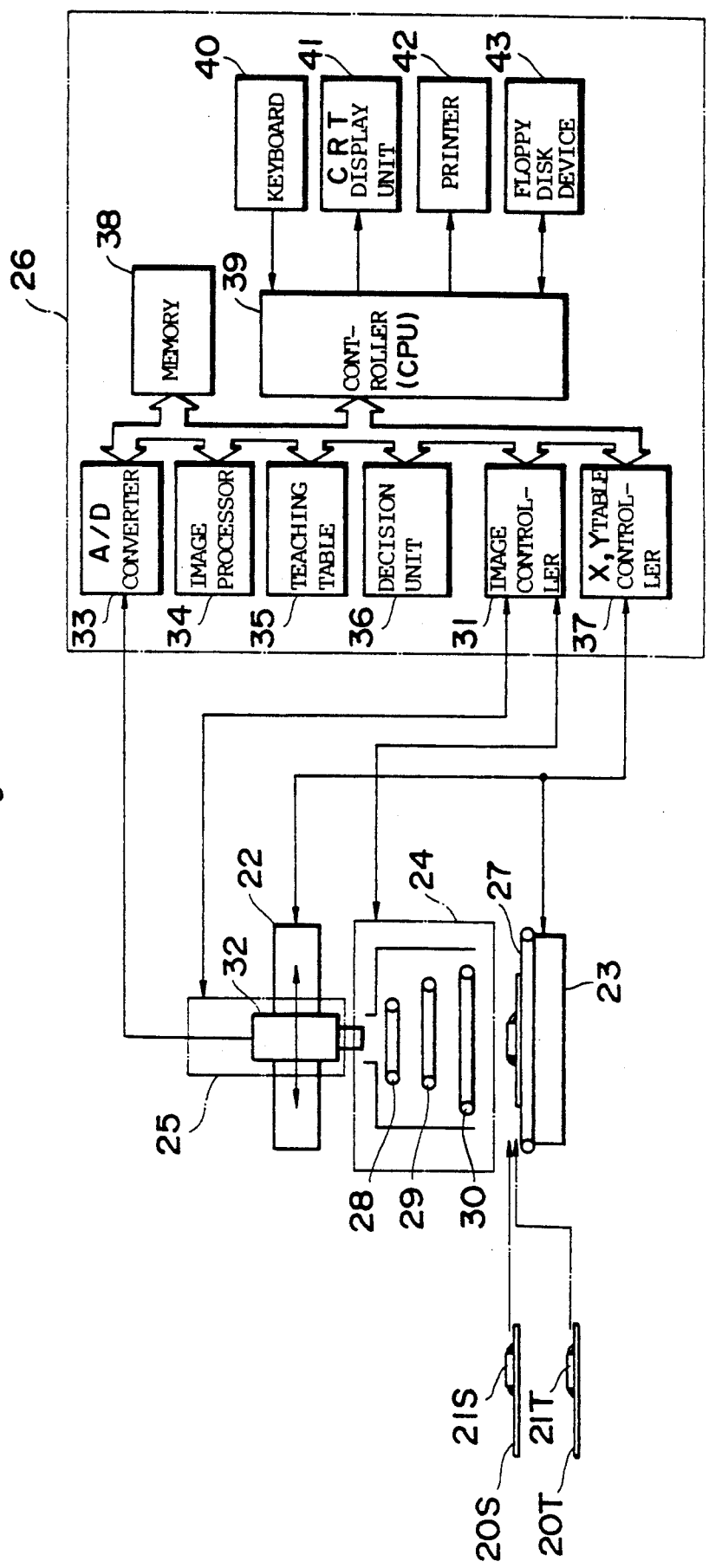
FIG. 4 is a block diagram illustrating the overall construction of a PC board inspecting apparatus in an embodiment of the present invention.

FIG. 4 illustrates the construction of a PC board inspecting apparatus in an embodiment of the present invention.

The apparatus for inspecting PC boards is for imaging a reference PC board (a positioning PC board) 20S, comparing feature parameters (criteria data) of an inspection zone of each part 21S on the reference PC board 20S, which parameters are obtained by processing the imaged data, with feature parameters(data to be inspected) of an inspection zone of each part 21T on a PC board 20T to undergo inspection, which parameters are obtained by imaging the PC board 20T to undergo inspection, and performing inspection to determine whether each part 21T is correctly mounted and soldered. The apparatus includes an X-axis table 22, a Y-axis table 23, a projecting unit 24, an image pickup unit 25 and a processing unit 26.

The X-axis table 22 and Y-axis table 23 are each equipped with a motor (not shown) controlled by a control signal from the processing unit 26. Driving these motors causes the X-axis table 22 to move the image pickup unit 25 in an X direction and causes the Y-axis table 23 to move a conveyor 27, which supports either the PC board 20S or 20T, in the Y direction.

The PC boards 20S and 20T are irradiated by the projecting unit 24 and imaged by the image pickup unit 25.

The projecting unit 24 is equipped with ring-shaped light-emitting elements 28, 29, 30 which respectively generate red light, green light and blue light, based on control signals from the processing unit 26, for irradiating the object of inspection at different angles of incidence. The PC board 20S or 20T is irradiated with light obtained by mixing the light of these three primary colors emitted by the light-emitting elements 28, 29, 30. The reflected-light image is converted into an electric signal by the image pickup unit 25. In this embodiment, the light-emitting elements 28, 29 and 30 employed are of a structure in which sources of white light are covered with colored transparent plates (color filters) of the colors red, green and blue, respectively. However, as long as the light-emitting elements generate light of the three primary colors, the invention is not limited to the above structure. For example, three ring-shaped color fluorescent lamps (red, green, blue) can be used, or use can be made of three ring-shaped neon tubes (red, green, blue).

In order to make it possible to detect, under illumination, information (part number, polarity, color code, etc.) relating to parts on the PC boards 20S, 20T or information (various marks, etc.) relating to a pattern on a PC board, the projecting unit 24 is designed in such a manner that perfectly white light is obtained when the light rays of the three hues emitted by the light-emitting elements 28, 29 and 30 are mixed. Specifically, the light-emitting elements 28, 29 and 30 are constituted by light-emitting elements which respectively emit a red-light spectrum, green-light spectrum and blue-light spectrum each having a light-emission energy distribution with respect to wavelength [a light-emission energy distribution in which wavelength is plotted along the horizontal axis and the peak thereof is set a 1 (100%)] that will give white light by mixing the colors. The quantity of the colored light outputted by each of the light-emitting elements 28, 29, 30 is adjusted by an imaging controller 31 in such a manner that the red light, green light and blue light emitted by the light-emitting elements 28, 29, 30 will yield white light upon being mixed.

The imaging unit 25 is equipped with a color television camera 32 situated above the projecting unit 24. Reflected light from the PC board 20S or 20T is converted into color signals R, G, B of the three primary colors by the color television camera 32, and the color signals are supplied to the processing unit 26.

The processing unit 26 comprises an A/D converter 33, an image processor 34, a teaching table 35, a decision unit 36, the imaging controller 31, an X, Y table controller 37, a keyboard 40, a CRT display unit 41, a printer 42, a floppy disk device 43, a memory 38 and a controller (CPU) 39. In the teaching mode, the processing unit 26 detects, through a method described later, the mounted position of each part 21S on the reference PC board 20S, the type of the mounted part, its mounted direction and inspection zone, and processes the color signals R, G, B regarding the reference PC board 20S, whereby hue patterns of the colors red, green and blue are detected with regard to the inspection zone of the part 21S whose soldered state is acceptable, thus forming feature parameters to fabricate a criteria data file. In the inspection mode, the processing unit 26 processes the color signals R, G, B regarding the PC board 21T that is to be inspected, detects similar hue patterns with regard to the inspection zone of each part 21T on this PC board, and forms feature parameters, thereby fabricating an inspected data file. The processing unit compares this inspected data file with the abovementioned criteria data file and, based upon the results of the comparison, automatically judges, with regard to a predetermined part 21T on the PC board 20T to be inspected, whether the soldered portion of this part is acceptable or not.

FIG. 5 shows a table illustrating the relationship between sectional views of solder 44 when soldering is acceptable, when a part is missing and when solder is inadequate, and the imaged pattern, red pattern, green pattern and blue pattern in each of these cases. Since a clear difference appears between these hue patterns, whether or not a part is present and whether or not soldering is acceptable can be judged.

Returning now to FIG. 4, the A/D converter 33, upon being supplied with the color signals R, G, B from the imaging unit 25, converts these signals into digital signals and applies the digital signals to the controller 39. The memory 38 includes a RAM used as a working area of the controller 39. The image processor 34 subjects the image data supplied via the controller 39 to image processing, creates the inspected data file and criteria data file and supplies these data files to the controller 39 and decision unit 36.

The teaching table 35 stores the criteria data file when this file is supplied to it from the controller 39 in the teaching mode. When the controller 39 outputs a transfer request in the inspection mode, the teaching table 35 responds to this request by reading out the criteria data file and supplying it to the controller 39, the decision unit 36, etc.

In the inspection mode, the decision unit 36 compares the criteria data file supplied by the controller 39 with the inspected data file transferred from the image processor 34, judges the acceptability of the soldered state with regard to the PC board 20T undergoing inspection, and outputs the result of judgment to the controller 39.

The imaging controller 31 is equipped with interfaces and the like for connecting the controller 39, projecting unit 24 and image pickup unit 25. The imaging controller regulates the quantity of light of each of the light-emitting elements 28, 29, 30 in accordance with commands from the controller 39 and performs control for maintaining balance among the colored light outputs of the television camera 32 in image pickup unit 25.

The X, Y table controller 37 is equipped with interfaces and the like for connecting the controller 39, X-axis table 22 and Y-axis table 23, and controls the X-axis table 22 and Y-axis table 23 based on the output of the controller 39.

The CRT display unit 41 is equipped with a cathode-ray tube (CRT). When supplied with image data, the results of judgment and keyed-in input data from the controller 39, the CRT display unit 41 displays these on a display screen. Upon being supplied with the results of judgment and the like from the controller 39, the printer 42 prints this out in a predetermined format. The keyboard 40 is equipped with various keys necessary for entering operating information as well as data relating to the reference PC board 20S and PC board 20T to be inspected. Information and data entered from the keyboard 40 are supplied to the controller 39.

The controller 39 includes a microprocessor and controls teaching and inspecting operations in line with a procedure described next.

First, an example of a teaching operation will be described with reference to FIG. 6. At the start of teaching, the controller 39 turns on the projecting unit 24 and image pickup unit 25 and arranges the imaging conditions and data processing conditions. At step 1 (indicated by "ST1" in the drawing), the operator manipulates the keyboard 40 to register the name of the PC board that is the object of teaching and enter the size of the PC board. Thereafter, at the next step 2, the operator sets the reference PC board 20S on the Y-axis table 23 and presses a START key. At step 3, the corners at the upper right and lower left of the reference PC board 20S are imaged as the origin of the PC board by the image pickup unit 25, and the corners are displayed on the CRT 41. The operator presses a specific key upon positioning a cursor at the position of each corner, whereupon the coordinates of the position of the cursor are entered as the coordinates of the corner. On the basis of the entered coordinate data, the controller 39 controls the X-axis table 22 and Y-axis table 23 to position the reference PC board 20S at an initial position.

Figure 9:
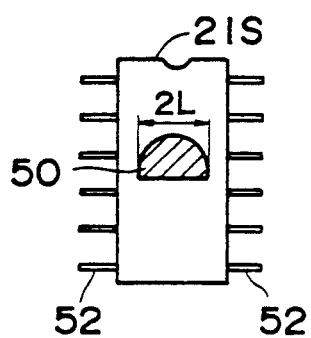
FIGS. 9 and 10 are plan views of parts showing labels in a state affixed thereto.

The reference PC board 20S is formed as one having acceptable mounted states by properly soldering the prescribed parts 21S at the prescribed part mounting positions. Labels 50, 51 of the kind shown in FIGS. 9 and 10 are affixed to the top surface of each part 21S substantially at the center thereof.

Figure 10:
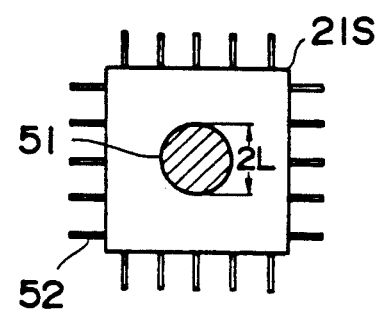

The labels 50, 51 are used for the purpose of teaching the mounted position of each part 21S, the type of the mounted part and its mounted direction (the direction of the part). In the case of this embodiment, a yellow hemispherical label 50 is affixed to a rectangular part 21S such as an SOP (small outlined package) having a number of leads on both longitudinal sides thereof, the label being affixed with its arcuate portion oriented in the mounting direction (the specific direction of the part 21S) (FIG. 9). A red circular label 51 is affixed to a square part 21S such as a QFP (quad flat package) having a number of leads 52 on all four of its sides (FIG. 10). A label of a different color or shape is affixed to a chip part (not shown) such as square chip. In this embodiment, the mounting position of a part is taught by the position at which the label is affixed, the type of part is taught by the color and shape of the label, and the mounted direction of the part is taught by the direction in which the label is affixed. Both the color and shape of a label are used to identify the type of part in order to prevent erroneous identification based on only a single item of information.

According to this embodiment, use is made of the reference PC board 20S on which the prescribed parts 21S have been properly soldered at the part mounting positions, and the label 50 or 51 is affixed to the top side of each part 21S. However, it is permissible to use a PC board on which a part has not been mounted and affix the label 50 or 51 to the PC board at the part mounting position. In this latter case it would be necessary to separately prepare a PC board for teaching feature parameters, described later, in addition to a PC board for teaching the part mounting positions.

Returning to FIG. 6, teaching processing with regard to part mounting position and mounted part type is started at step 4 when the reference PC board 20S is positioned at the initial position.

Figure 7:
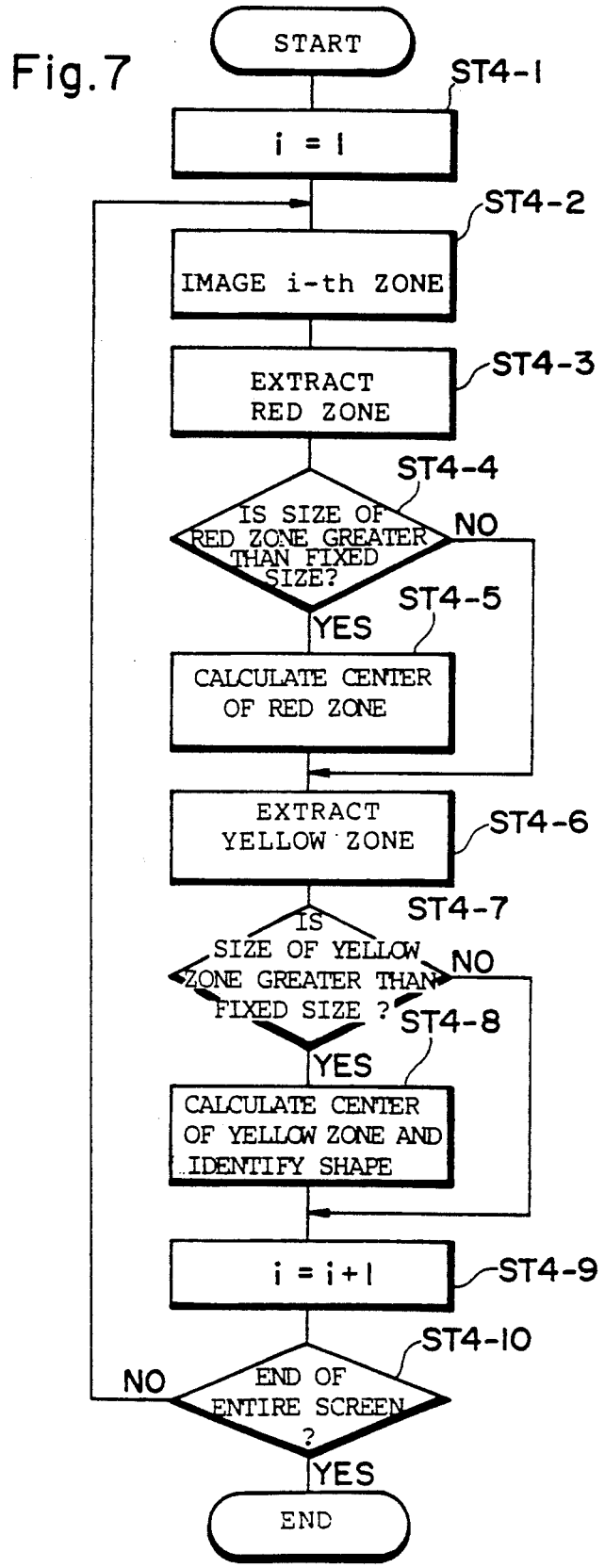

FIG. 7 illustrates the details of this teaching processing. At step 4-1, "1" is initially set in a counter i of the controller 39 for counting imaging zones. A zone on the reference PC board 20S corresponding to the content of the counter i is imaged and the initial frame is produced (step 4-2).

Figure 11:
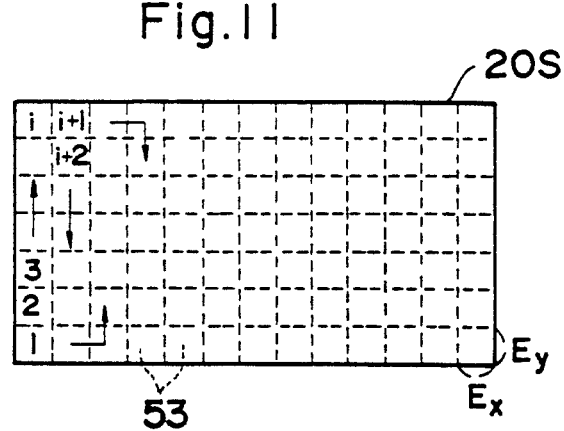
FIG. 11 is an explanatory view showing partitioned regions on a PC board and a processing sequence.

As shown in FIG. 11, the area of the PC board 20S is partitioned into a number of rectangular zones 53 each having a length and width of $E_x \times E_y$, and each rectangular zone 53 corresponds to the size of one frame. First, a frame of the zone 53 at the lower left is produced and the processing of step 4-3 to step 4-10 is executed. Thereafter, similar processing is executed repeatedly with regard to each of the rectangular zones 53 in accordance with the arrows shown in the drawing.

First, at step 4-3, extraction of red zones is performed in the image processor 34.

Letting a pixel position on an image be represented by (x,y), and letting the gray-level values (luminosities) of the primary colors of a pixel at coordinates (x,y) be R(x,y), G(x,y) and B(x,y), the hue values r(x,y), g(x,y) and b(x,y) of the colors red, green and blue will be given by the following equations (2), (3) and (4), respectively:

$$r(x,y) = [R/(R+G+B)] \times 100 \quad (2)$$

$$g(x,y) = [G/(R+G+B)] \times 100 \quad (3)$$

$$b(x,y) = [B/(R+G+B)] \times 100 \quad (4)$$

The processing of step 4-3 for extracting red zones is executed by extracting pixels which satisfy $R(x,y) \geq T_1$ and $r(x,y) \geq T_2$ (where $T_1$, $T_2$ are fixed values that are preset).

FIGS. 12a through 12c illustrate a red zone 55 extracted on an image 54. FIG. 12a illustrates the red zone extracted at the central portion of the image 54, and FIGS. 12b, 12c show the red zone 55 extracted at peripheral portions of the image 54.

Next, at step 4-4, a rectangle abcd circumscribing the red zone 55 is formed by tracing the contour of the extracted red zone 55, and it is determined whether the lengths of two sides of the circumscribing rectangle are both greater than a radius L of the label 51. In this way it is determined whether the size of the red zone 55 is greater than a fixed size, namely whether the red zone 55 is one corresponding to the image of the red label 51.

If the decision rendered at step 4-4 is NO, then step 4-5 is skipped and the program proceeds to step 4 6. If the decision at step 4-4 is YES, however, the controller 39 calculates, at the next step 4-5, the coordinates of the center of the red zone 55 in conformity with each of the cases shown in FIGS. 12a through 12c.

Specifically, FIG. 12a illustrates a case in which the extracted red zone 55 does not contact any of the sides of the image 54. In this case, the position of the center of the circumscribing rectangle abcd is adopted as the position of the center of label 51.

FIG. 12b illustrates a case in which the extracted red zone 55 contacts any one side of the image 54. In this case, a length 2L from one point a on the circumscribing rectangle abcd in the direction of line segment ab is taken to form a rectangle ab'c'd, and the position of the center of this rectangle is adopted as the position of the center of label 51.

FIG. 12c illustrates a case in which the extracted red zone 55 contacts two sides of the image 54. In this case, lengths 2L from one point a on the circumscribing rectangle abcd in the directions of line segments ab, ad are taken to form a rectangle ab'c'd', and the position of the center of this rectangle is adopted as the position of the center of label 51.

When the coordinates of the center position of the label 51 have been found, the controller 39 transforms these coordinates into coordinates in the coordinate system of the reference PC board 20S and adopts these new coordinates as the position of the part.

Next, the image processor 34 extracts a yellow zone at step 4-6. Processing for extraction of this yellow zone is executed by extracting pixels which satisfy $R(x,y) \geq T_3$, $r(x,y) > T_4$, $G(x,y) \geq T_5$, $g(x,y) \geq T_6$, $B(x,y) < T_7$, $b(x,y) < T_8$, (where $T_3$ through $T_8$ are fixed values that are preset).

FIGS. 13a through 13c illustrate a yellow zone 57 extracted on an image 56. FIG. 13a illustrates the yellow zone extracted at the central portion of the image 56, and FIGS. 13b, 13c show the yellow zone 57 extracted at peripheral portions of the image 56.

Next, at step 4-7, a circumscribing rectangle abcd is formed by tracing the contour of the yellow zone 57, and it is determined whether the length of one side of the circumscribing rectangle is greater than a radius L of the label 50 and whether the length of one other side is greater than L/2. In this way it is determined whether the size of the yellow zone 57 is greater than a fixed size, namely whether the yellow zone 57 is one corresponding to the image of the yellow label 50.

If the decision rendered at step 4-7 is NO, then step 4-8 is skipped and the program proceeds to step 4-9. When the decision at step 4-7 is YES, the controller 39 calculates, at the next step 4-8, the coordinates of the center of the yellow zone 57 in conformity with each of the cases shown in FIGS. 13a through 13c.

Specifically, FIG. 13a illustrates a case in which the extracted yellow zone 57 does not contact any of the sides of the image 56. In this case, the position of the center of the circumscribing rectangle abcd is adopted as the position of the center of label 50.

FIG. 13b illustrates a case in which the extracted yellow zone 57 contacts any one side of the image 56. In this case, a rectangle (indicated by the dashed line) is formed such that one side of the circumscribing rectangle abcd will be L and the other side L/2, and the position of the center of this rectangle is adopted as the position of the center of label 50.

FIG. 13c illustrates a case in which the extracted yellow zone 57 contacts two sides of the image 56. In this case also, a rectangle (indicated by the dashed line) is formed such that one side of the circumscribing rectangle abcd will be L and the other side L/2, and the position of the center of this rectangle is adopted as the position of the center of label 50.

When the coordinates of the center position of the label 50 has been found, the controller 39 transforms these coordinates into coordinates in the coordinate system of the reference PC board 20S and adopts these new coordinates as the position of the part.

The controller 39 calculates the coordinates of the position G of the center of gravity of the yellow zone 57 and, based on the positional relationship between the position G of the center of gravity and the abovementioned center position O, detects in which direction the arcuate portion of the yellow label 50 is oriented. For example, in a case where the coordinates of the center position O of the circumscribing rectangle abcd are $(x_0, y_0)$ and the coordinates of the center-of-gravity position G of the yellow zone 57 are $(x_G, y_G)$, it is judged that the arcuate portion of the yellow label 50 is oriented in the leftward direction (the negative direction along the X axis) if the relations $y_0 = y_G$, $x_0 < x_G$ hold.

When extraction of the red zone 51 or yellow zone 50 and the calculation of the center positions of these zones are thus completed, the counter i is incremented at step 4-9 and it is determined (step 4-10) based on the contents of the counter i whether processing with regard to all rectangular zones 53 on the reference PC board 20S has ended. If the decision rendered is NO, then the program returns to step 4-2 and processing similar to the foregoing is executed with regard to the rectangular zones 53 designated on the reference PC board 20S by the value of the count in counter i.

FIG. 15a illustrates a display screen of the CRT unit 41 when the foregoing processing proceeds. Displayed in a predetermined region 58 of the screen are detected positions 59 (indicated by "+") of rectangular parts 21S on which the yellow labels 50 have been affixed, and detected positions 60 (indicated by ".") of square parts 21S on which the red labels 51 have been affixed.

Figure 6:
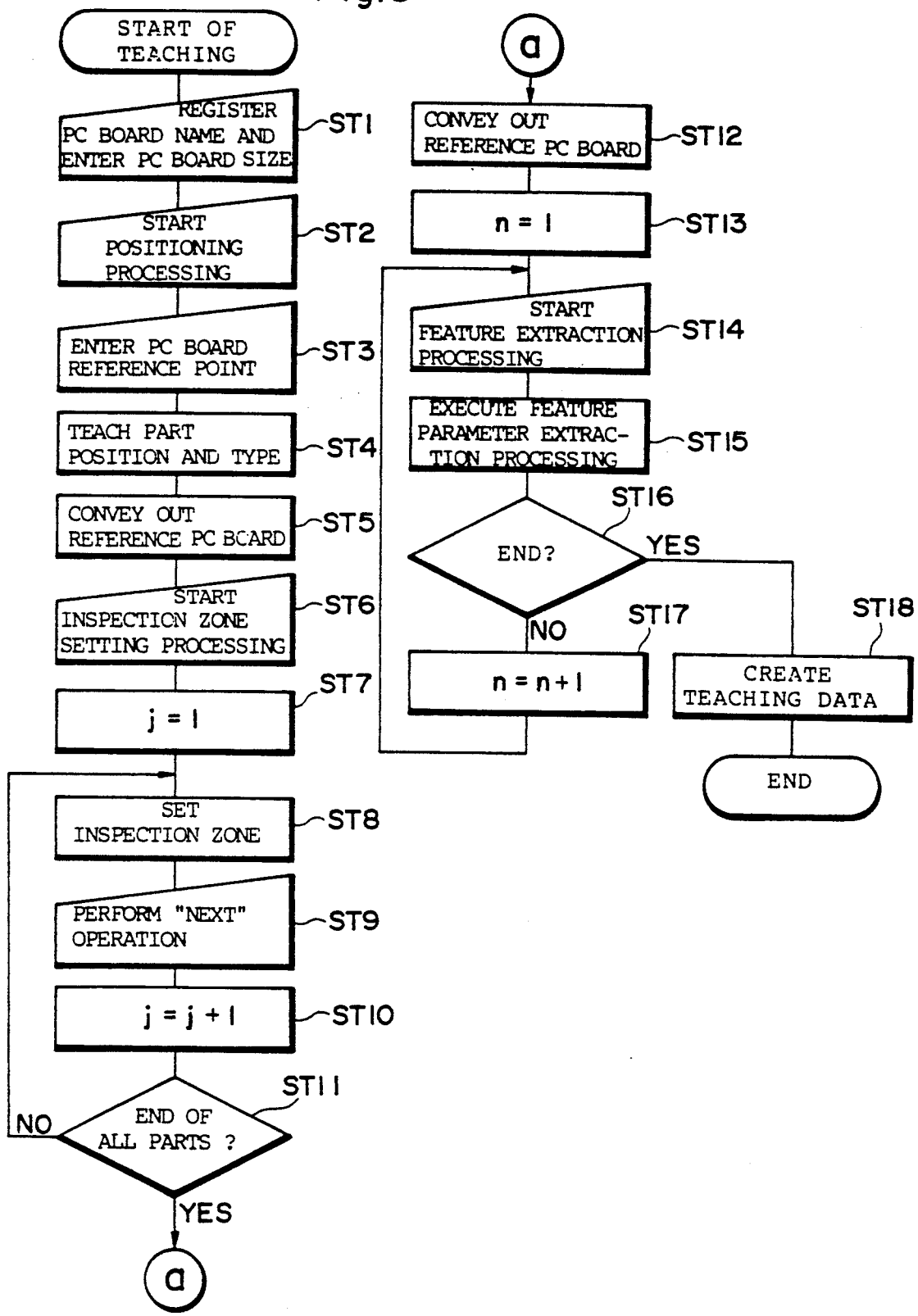
FIGS. 6 and 7 are flowcharts showing a teaching processing procedure.

If the decision rendered at step 4-10 is YES, processing for teaching part position and type is completed, the program proceeds to step 5 in FIG. 6, and the reference PC board 20S is conveyed out.

At the next step 6 in FIG. 6, the operator sets the reference PC board 20S, on which prescribed parts have been properly mounted at predetermined positions, on the Y-axis table 23 and then presses the START key to start teaching processing for the purpose of setting a inspection zone. In this embodiment, the PC board used in the teaching processing of the earlier step 4 is re-utilized as the reference PC board 20S for setting inspection zone. However, it goes without saying that the present invention is not limited to this arrangement.

First, at step 7, one is initially set in a counter j of the controller 39 for counting the number of parts. Based on the part-position data obtained by earlier teaching, the controller 39 controls the X-axis table 22 and Y-axis table 23 to position the first part 21S within the field of the television camera 32 and causes the part to be imaged.

FIGS. 14a and 14b concretely illustrate an inspection-zone setting method with regard to an image 61, of a rectangular part such as an SOP, obtained by this imaging. This method entails initially setting, with respect to the image 61, rectangular processing zones 62A, 62B, indicated by the chain lines in FIG. 14a, corresponding to both side portions of the SOP part, automatically extracting lands 63 on the PC board by performing projection processing within each of the processing zones 62A, 62B, thereafter obtaining circumscribing rectangles 68A, 68B which include the lands 63, as shown in FIG. 14b, and setting rectangular inspection zones 64A, 64B by enlarging the circumscribing rectangles a predetermined width in all directions. This processing for setting inspection zones will be described in detail later.

Though a method of setting inspection zones with regard to the SOP part will be exemplified here, it goes without saying that the setting of inspection zones is carried out by a method conforming to this setting method with regard to other parts as well.

After the setting of inspection zones is thus completed for the first part, the operator presses a NEXT key on the keyboard 40 at step 9, whereupon the counter j is incremented (step 10) and it is determined (step 11), based on the contents of the counter j, whether the setting of inspection zones has been performed for all of the parts. If the decision rendered at step 11 is NO, the next part is imaged and processing similar to the foregoing is executed.

FIG. 15b illustrates a display screen of the CRT display unit 41 when the foregoing processing proceeds. Whenever inspection zones of the parts are set at the detected positions 59, 60 of these parts in a region 58, the display of the positions 59, 60 is changed over to displays 65, 66 conforming to the shapes and sizes of the parts.

When the decision at step 11 becomes YES as a result of repeatedly executing the same processing with regard to all parts, the reference PC board 20S is conveyed out (step 12), then the program proceeds to processing for teaching characteristic parameters.

First, at step 13, a counter n in the controller 39 for counting the number of PC boards is initially set to one, after which the operator sets the first reference PC board 20S (one on which prescribed parts have been properly mounted at predetermined locations and soldered into place) on the Y-axis table 23 and presses the START key of the keyboard 40 at step 14, whereupon the controller 39, based on the part-position data, obtained by the earlier teaching operation, and the inspection-zone data, controls the Y-axis table 23 at step 15 to successively position the field of the television camera 32 at each part and image each part.

The color signals R, G, B of the three primary colors obtained by imaging are converted into digital data by the A/D converter 33 and these digital data are stored in the memory 38 in realtime. Next, the controller 39 extracts each land within the inspection zones of each part obtained by earlier teaching, reads the image data of each hue relating to these lands out of the memory 38 and transfers the image data to the image processor 34. The image processor 34 binarizes the image data of each hue at a suitable threshold value hue by hue, detects the normal soldered state of each of the lands as patterns of the colors red, green and blue, and calculates the feature of these patterns as feature parameters.

FIG. 21a illustrates a lead 52 properly soldered to a land 70 with regard to the part 21S mounted on the reference PC board 20S. Here a sufficient amount of solder 71 is placed on the land 70 and covers the land 70 up to a tip 70a thereof.

When such a normally soldered region is imaged, a pattern of three primary colors such as shown in FIG. 22a appears, in which the red zone at the tip portion 70a appears particularly red owing to the presence of the solder 71.

Accordingly, the red hue value is obtained with regard to the red zone of the tip portion 70a and this is adopted as a feature parameter.

When extraction of a plurality of feature parameters is completed for each and every part with regard to the first reference PC board 20S, this circuit board is conveyed out. Thereafter, the counter n is incremented to designate the second reference PC board, and processing for feature parameter extraction is executed through a procedure similar to that described above.

When processing for extracting feature parameters ends for a predetermined number (n) of reference PC boards 20S, a YES decision is rendered at step 16 and the program proceeds to step 18. In order to obtain an average feature quantity with regard to each part, the controller 39, at step 18, calculates the mean value and a standard deviation by statistically processing each feature parameter regarding the n-number of reference PC boards 20S, creates a criteria data file in which a range corresponding to (the mean value)±(a constant)×(the standard deviation) is adopted as the normal range, stores this in the teaching table 35, executes a correction of the data whenever necessary, and terminates teaching.

FIG. 23 illustrates a distribution of data obtained from n-number of reference PC boards 20S with regard to red hue values of the tip portion 70a of land 70. A correct range of a feature parameter is stipulated based on mean value and standard deviation of the red hue values calculated by statistical processing.

When teaching is completed in the foregoing, the apparatus for PC board inspection enters a state in which it is possible to perform automatic inspection of the PC board 20T, which is to undergo inspection, following the soldering of parts thereon.

Figure 8:
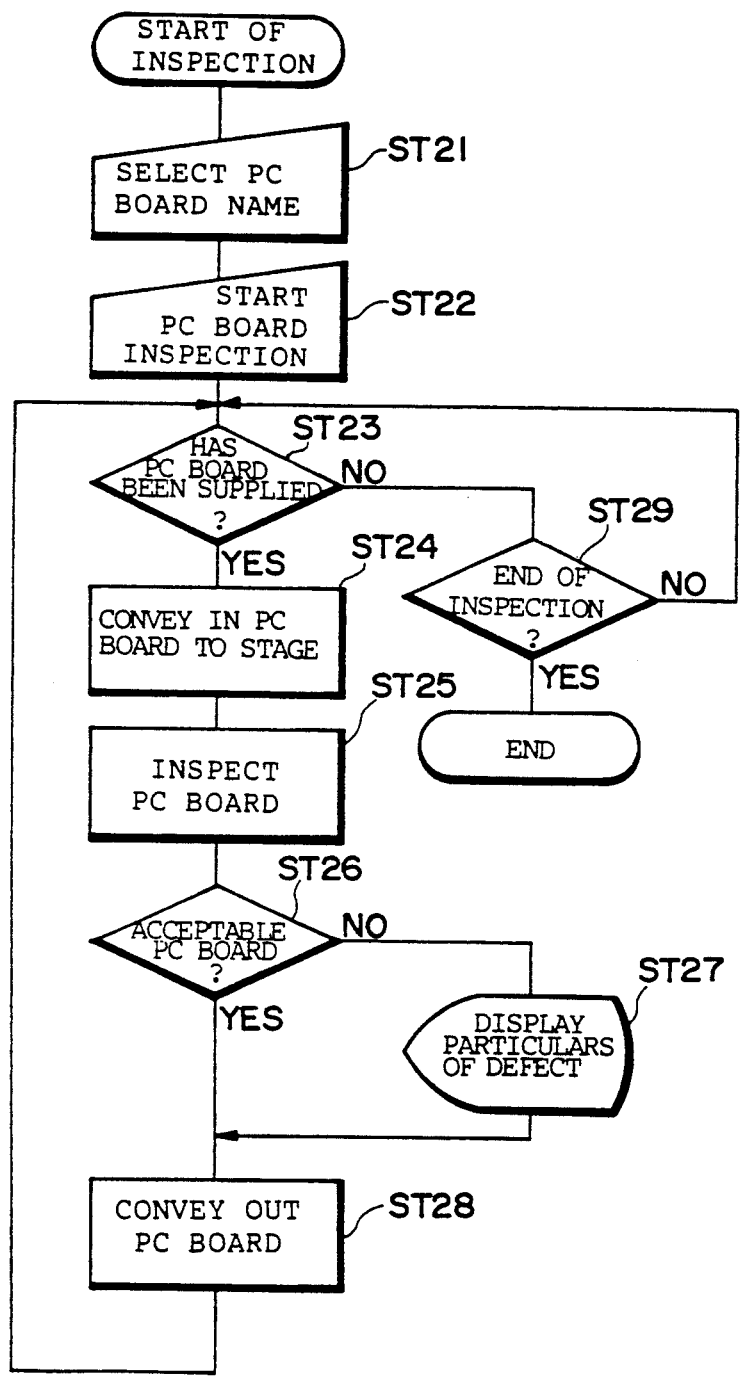
FIG. 8 is a flowchart showing the procedure of inspection processing.

The operator effects a transition to the inspection mode shown in FIG. 8 and, at steps 21 and 22, selects the name of the PC board to be inspected and performs an operation to start the inspection of the PC board.

At the next step 23, it is checked to determine whether the PC board 20T to be inspected has been supplied to the PC board inspecting apparatus. If the circuit board has been supplied, the conveyor 27 is driven into operation to convey the PC board 20T in to the Y-axis table 23, and inspection of the PC board begins (steps 24, 25).

At step 25, the controller 29 controls the X-axis table 22 and Y-axis table 23 to position the field of the television camera 32 with respect to the first part 21T on the PC board to be inspected, causes this part to be imaged, automatically extracts each land region within the inspection zones, calculates the feature parameters of each land region and creates an inspected data file. The controller 39 then transfers the inspected data file to the decision unit 36, and causes to compare the inspected data file with the abovementioned criteria data file, and the acceptability of soldered portions to be judged for the first part 21T.

FIG. 21b illustrates a part 21T having a soldering defect. Only a very small amount of solder 71 resides on the land 70, and the tip portion 70a of the land 70 is exposed because the solder 71 is missing.

When a soldered region in such a state is imaged, a pattern in the three primary colors similar to the pattern for the normal state appears, as shown in FIG. 22b. However, here the red zone of the tip portion 70a is dull owing to the missing solder 71.

Accordingly, when the red hue value regarding the red zone of the tip portion 70a of such a defective part is obtained as the feature parameter, this value falls outside the normal range shown in FIG. 23.

When such an inspection is repeatedly executed for all parts 21T on the PC board 20T undergoing inspection and the results thereof are indicative of a soldering defect, the defective part and the particulars of the defect are displayed on the display unit 41, these are printed out by the printer 42, and thereafter the inspected PC board 20T is conveyed out from the inspection position (steps 27, 28).

FIG. 15c illustrates a display screen of the CRT display unit 41 displaying the results of judgment. In FIG. 15c, the above-described part displays 65, 66 appear in the region 58, and a part 65a with the soldering defect is displayed in a specific color. Further, the defect particulars regarding the improperly soldered part designated by the operator are displayed in a display region 67 below the region 58. A part designated by the operator appears clearly on the screen in a color different from that indicating the improperly soldered part 65a.

The details of the method (step 8 in FIG. 6) for setting inspection zones described briefly with reference to FIGS. 14a and 14b will now be set forth.

Figure 16:
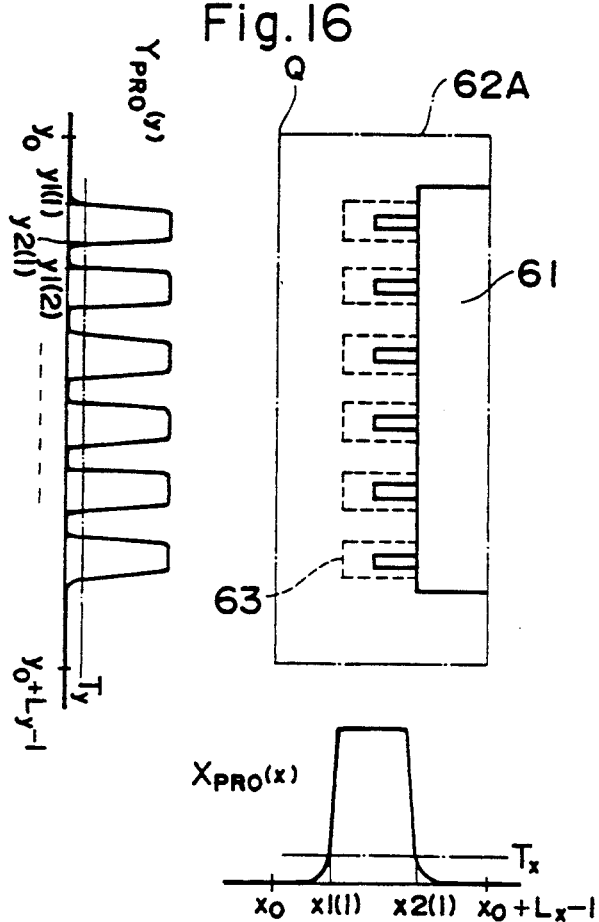
FIG. 16 is an explanatory view showing a method of projection processing.

FIG. 16 illustrates a method of projection processing in one processing zone 62A. The processing zone 62A (62B) is such that the longitudinal and transverse sides thereof are initially set to predetermined lengths, and the orientation of the zone is decided in dependence upon part direction obtained by the earlier teaching procedure with regard to the image 61.

Letting the position of each pixel constituting the image 61 be represented by coordinates (x,y), and letting the gray-level values of the three primary-color color signals of the pixel at coordinates (x,y) be $R(x,y)$, $G(x,y)$ and $B(x,y)$, respectively, the hue values $r(x,y)$, $g(x,y)$ and $b(x,y)$ of the colors red, green and blue will be given by the abovementioned Equations (2) through (4), respectively.

In order to extract a land 63 in the processing zone 62A, each gray-level value and each hue value are calculated with regard to all pixels contained in the processing region 62A, and it is determined based on these values whether a pixel is one constituting the land 63.

More specifically, when a pixel of interest satisfies the relation $R(x,y) \geq T_{10}$ and $r(x,y) \geq T_{11}$, or $G(x,y) \geq T_{12}$ and $g(x,y) \geq T_{13}$, or $B(x,y) \geq T_{14}$ and $b(x,y) \geq T_{15}$. the pixel is regarded as one constituting the land 63 and weighting of $W(x,y)=1$ is applied to this pixel. Otherwise, the pixel is regarded as a pixel other than one constituting the land 63, and weighting of $W(x,y)=0$ is applied to this pixel. $T_{10}$, $T_{11}$, $T_{12}$, $T_{13}$, $T_{14}$ and $T_{15}$ are preset fixed values. The total sum of $W(x,y)$ is calculated in accordance with the following equations with regard to each row and column of the image 61:

$$X_{PRO}(x) = \sum_{y=y_0}^{y_0+L_y-1} W(x,y) \quad (5)$$

where $y_0 \leq y \leq y_0 + L_y - 1$ $$Y_{PRO}(y) = \sum_{x=x_0}^{x_0+L_x-1} W(x,y) \quad (6)$$

where $x_0 \leq x \leq x_0 + L_x - 1$

Here $(x_0,y_0)$ represents the coordinates of the upper-left corner Q of the processing zone 62A, and $L_x$, $L_y$ represent the respective lengths of two sides of the processing zone 62A. $X_{PRO}(x)$ and $Y_{PRO}(y)$ are graphed in FIG. 16.

Next, the maximum values of $X_{PRO}(x)$ and $Y_{PRO}(y)$ are taken as $\{X_{PRO}(x)\}_{MAX}$, $\{Y_{PRO}(y)\}_{MAX}$, respectively, and threshold values $T_x$, $T_y$ are found from the following equations, respectively:

$$T_x = (1/6)\{X_{PRO}(x)\}_{MAX} \quad (7)$$

$$T_y = (1/6)\{Y_{PRO}(y)\}_{MAX} \quad (8)$$

$X_{PRO}(x)$ and the threshold value $T_x$ are compared, and the x coordinates for which the two coincide are taken as x1(1), x2(1), x1(2), x2(2), ..., x1(i), x2(i) in order of increasing value. Further, $Y_{PRO}(x)$ and the threshold value $T_y$ are compared, and the y coordinates for which the two coincide are taken as y1(1), y2(1), y1(2), y2(2), ..., y1(j), y2(j) in order of increasing value (where i, j are not relation to the counters mentioned above).

Next, a length $L_i$ and a length $L_j$ are found in accordance with following Equations (9) and (10), and from among rectangular regions [x1(i), y1(j), Li, Lj] defined by coordinates [x1(i), y1(j)] and lengths $L_i$, $L_j$, one which satisfies the following Equations (11) and (12) is set as the land 63:

$$L_i = x_2(i) - x_1(i) + 1 \quad (9)$$

$$L_j = y_2(j) - y_1(j) + 1 \quad (10)$$

$$L_i \geq W_x \quad (11)$$

$$L_j \geq W_y \quad (12)$$

Here $W_x$, $W_y$ are fixed values.

Similarly, with regard to the other processing zone 62B, the land 63 is extracted, after which rectangles 68A, 68B circumscribing each land 63 are obtained and the rectangles 68A, 68B are enlarged by a predetermined width to set the rectangularly shaped inspection zones 64A, 64B.

Figure 17A:
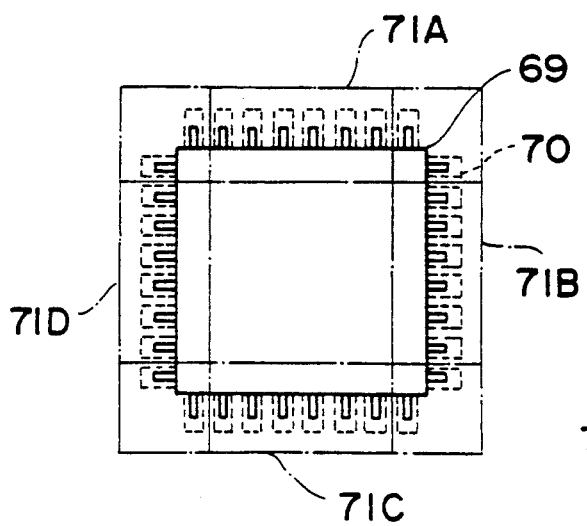
Figure 17B:
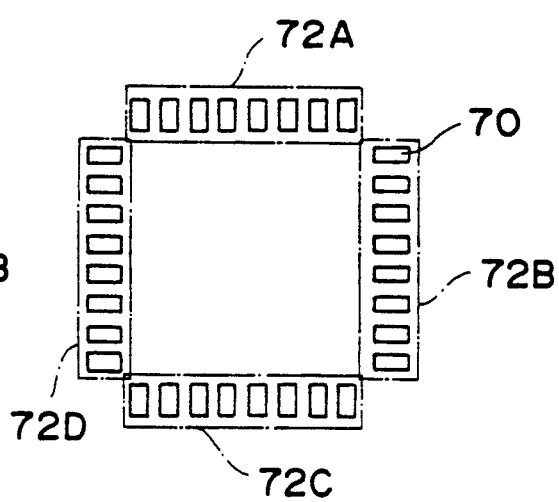

FIGS. 17a and 17b concretely illustrate a method of setting inspection zones with regard to the image 69 of a square part. In this case, rectangularly shaped processing zones 71A through 71D indicated by the chain lines are initially set to correspond to the four sides of the image 69 of the part, lands 70 on the PC board are automatically extracted by executing projection processing similar to the foregoing within each processing zone, thereafter a circumscribing rectangle which includes the lands 70 is found with regard to each side, and this is enlarged by a predetermined width in all directions to set the rectangularly shaped inspection zones 72A through 72D shown in FIG. 17b. The above-mentioned processing zones 71A through 71D and processing zones 73A through 73H described later are of course those in which the longitudinal and transverse side have been initially set to predetermined lengths.

FIG. 18a through 18e illustrate a method of setting inspection zones for a case where a square part is large in size and the entire figure of the part will not fit into the single image 69.

Figure 19:
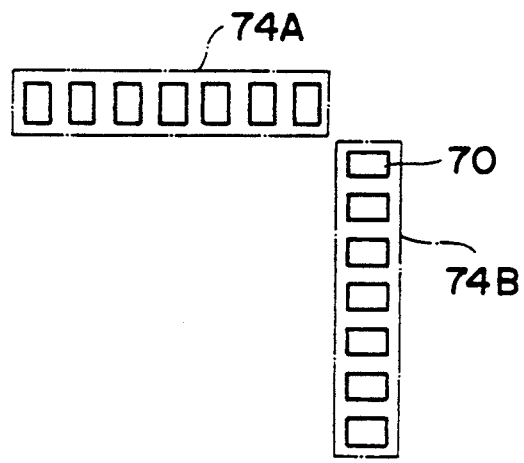

In this case, starting from the state (shown in FIG. 18a) in which the center O of the part obtained by the teaching operation described earlier is situated at the center of the screen, the X-axis table 22 and the Y-axis table 23 are driven to move the field of the television camera 32, whereby the upper-right corner and each row of lands 70 on the right side as well as the upper side are adjusted so as to enter the screen, as shown in FIG. 18b. At this time traveling distances $x_T$, $y_T$ in the X and Y directions are stored in memory. Rectangularly shaped processing zones 73A, 73B indicated by the chain lines are initially set at the positions of the right side and upper side of the part in the image 69, the lands 70 on the PC board are automatically extracted by performing projection processing within each processing zone, circumscribing rectangles which contain the lands 70 are subsequently found with regard to each side, and these rectangles are enlarged by a predetermined width in all directions to set the rectangularly shaped inspection zones 74A, 74B shown in FIG. 19.

Next, the Y-axis table 23 is driven to move the field of the television camera 32 by $-2y_T$, whereby the lower-right corner and each row of lands 70 on the right side as well as the lower side are adjusted so as to enter the screen, as shown in FIG. 18c, and processing similar to the foregoing is executed with regard to processing zones 73C, 73D.

Next, the X-axis table 22 is driven to move the field of the television camera 32 by $-2x_T$, whereby the lower-left corner and each row of lands 70 on the left side as well as the lower side are adjusted so as to enter the screen, as shown in FIG. 18d, and processing similar to the foregoing is executed with regard to processing zones 73E, 73F.

Further, the Y-axis table 23 is driven to move the field of the television camera 32 by $+2y_T$, whereby the upper-left corner and each row of lands 70 on the left side as well as the upper side are adjusted so as to enter the screen, as shown in FIG. 18e, and processing similar to the foregoing is executed with regard to processing zones 73G, 73H.

Figure 20A:
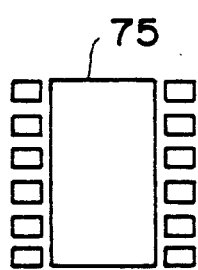
FIGS. 20a and 20b are views illustrating the set states of part size.
Figure 20B:
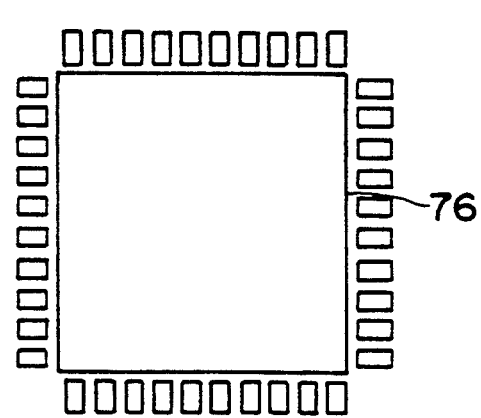

When the setting of inspection zones is thus completed with regard to one part, the operator performs a correction operation if required, after which the sizes (indicated by the bold lines 75, 76 in FIGS. 20a and 20b) of the part bodies (the package portion) of the parts are obtained based on the land regions, and the parts corresponding to these sizes are displayed on the display screen of the CRT display unit 41.

As set forth above, FIG. 15b illustrates the display screen of the CRT display unit 41 at this time. The displays of the part detection positions 59, 60 within the prescribed display region 58 are changed over to part displays 65, 66 conforming to the part sizes whenever processing for setting the inspection zones of the parts ends.

Figure 24:
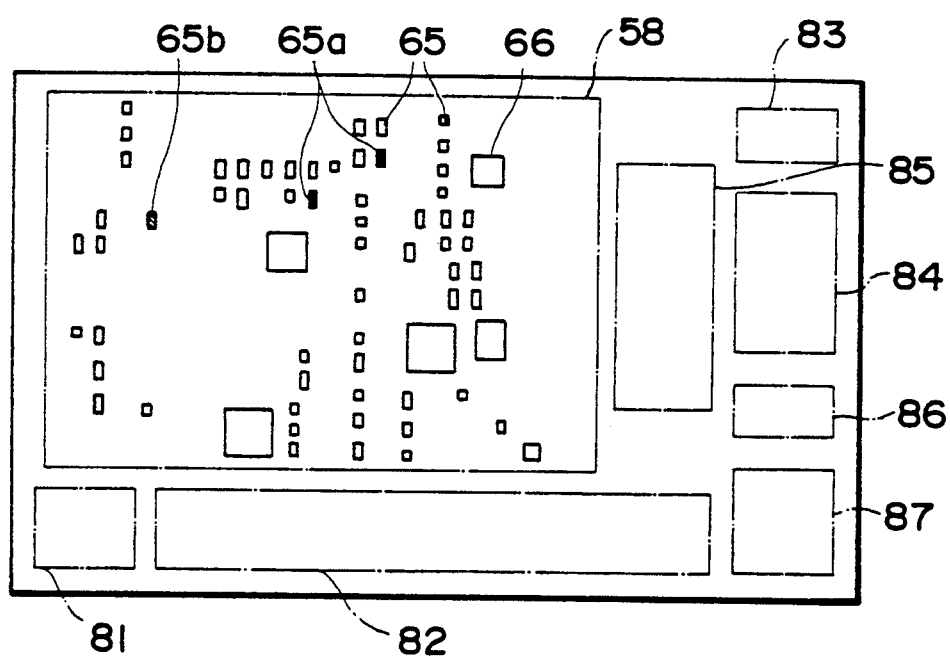
FIG. 24 is an explanatory view showing a display screen of a CRT display unit.

An example of the screen displaying the results of inspection is illustrated in FIG. 15c, as set forth above. FIG. 24 shows another example of a screen displaying the results of inspection.

In FIG. 24, the display screen of the CRT display unit 41 is divided into a plurality of screen areas. In addition to the screen area 58 for displaying the positions of parts on the PC board, there are provided therebelow a screen area 81 for displaying the state of the system, and a screen area 82 for displaying a key operation guide as well as the particulars of a fault possessed by a defective part. Further, provided at positions on the right side are a screen area 83 indicating the name of a mode, screen areas 84, 85 which display a PC board menu and the contents of a sub-menu, a screen area 86 which displays the date, and a screen area 87 which displays a system message.

The positions of the part on the PC board are indicated in the screen area 58 by the displays 65, 66 of the shapes conforming to the part shapes. With regard to a part judged to be an "acceptable part" by inspection, the part is displayed in a predetermined hue (e.g., white), whereas a part judged to be an "unacceptable part" is changed over to the shape display 65a of a different hue (e.g., red).

The screen area 82 displays, as the particulars of a defect of a defective part, the part number, the number of a lead with a soldering fault, a number between leads at which a solder bridge or solder ball is present, a code indicating whether a mounting defect is present, and a code or characters indicating the particulars of a soldering defect, etc. In the case of this embodiment, the information regarding one defective part is displayed in area 82 and the display is changed over whenever a predetermined key on the keyboard 40 is pressed, whereby the defect particulars of other defective parts may be displayed in successive fashion. In this case, with regard to a defective part being displayed in the screen area 82, the display 65b is implemented in screen area 58 in still another different color (e.g., yellow). Accordingly, establishing correspondence between the defective part and the part position and verification of the particulars of the defect are greatly facilitated.

This embodiment employs a system in which the particulars of a defect are displayed in one screen per part. However, the invention is not limited to this embodiment, for it is possible to display defect particulars regarding all defective parts together on one screen in the form of a table.

Another method of displaying detected soldered states of parts on a PC board will now be described.

Described first will be display of image data obtained in the feature-extraction processing at step 15 in FIG. 6. In feature-extraction processing as set forth above, the normally soldered state of a land is detected as patterns of the colors red, green and blue, and the features of these patterns are calculated as feature patterns.

In order to detect the soldered state of a land as patterns of the colors red, green and blue, detection of a red pattern is performed by extracting pixels which satisfy the relations $R(x,y) \geq T_1$ and $r(x,y) \geq T_2$. Further, detection of a green pattern is performed by extracting pixels which satisfy the relations $G(x,y) \geq T_{23}$ and $g(x,y) \geq T_{24}$, and detection of a blue pattern is performed by extracting pixels which satisfy the relations $B(x,y) \geq T_{25}$ and $b(x,y) \geq T_{26}$. Here $T_{23}$ through $T_{26}$ are fixed values preset by the operator.

When each of the patterns of the colors red, green and blue constituting each land are thus detected, the image of the part is displayed on the CRT display unit 41, with the pattern regions of each of the colors being respectively represented by corresponding colors of a fixed hue (these colors shall be referred to as "pseudo colors" hereinafter). For example, the pseudo color of the color red can be red of a fixed hue or another color.

Figure 26A:
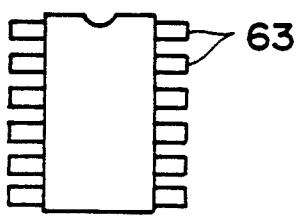
FIGS. 26a and 26b are, respectively, a view showing a display screen of a CRT display unit at the time of teaching and an explanatory view showing a portion of the display screen in enlarged form.
Figure 26B:
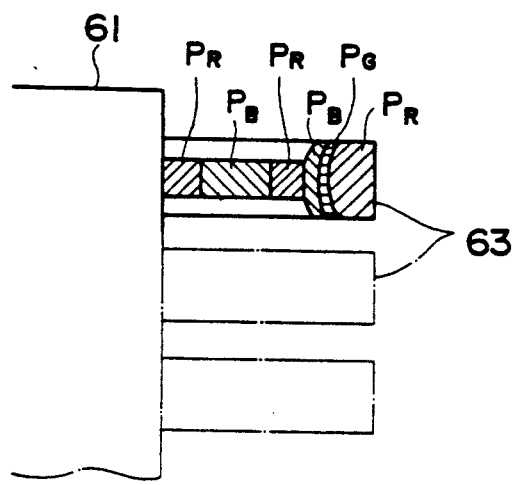

FIG. 26a illustrates a display screen of the CRT display unit 41. As shown in the enlarged view of FIG. 26b, each land 63 is composed of pattern regions $P_R$ (indicated by lines sloping downward to the left) in a pseudo color of the color red, a pattern region $P_G$ (indicated by horizontal lines) in a pseudo color of the color green, and pattern regions $P_B$ (indicated by lines sloping downward to the right) in a pseudo color of the color blue.

When processing for extracting feature parameters ends with regard to a predetermined number (n) of the reference PC boards 20S as described above, a YES decision is rendered at step S16 and the program proceeds to step 18. In order to obtain mean feature quantities regarding all parts, the controller 39 obtains mean-value data at step 18 by statistically processing feature parameters regarding n-number of the reference PC boards 20S, creates a criteria data file based on these mean-value data, and stores the file in the teaching table 35, as described earlier.

Figure 25:
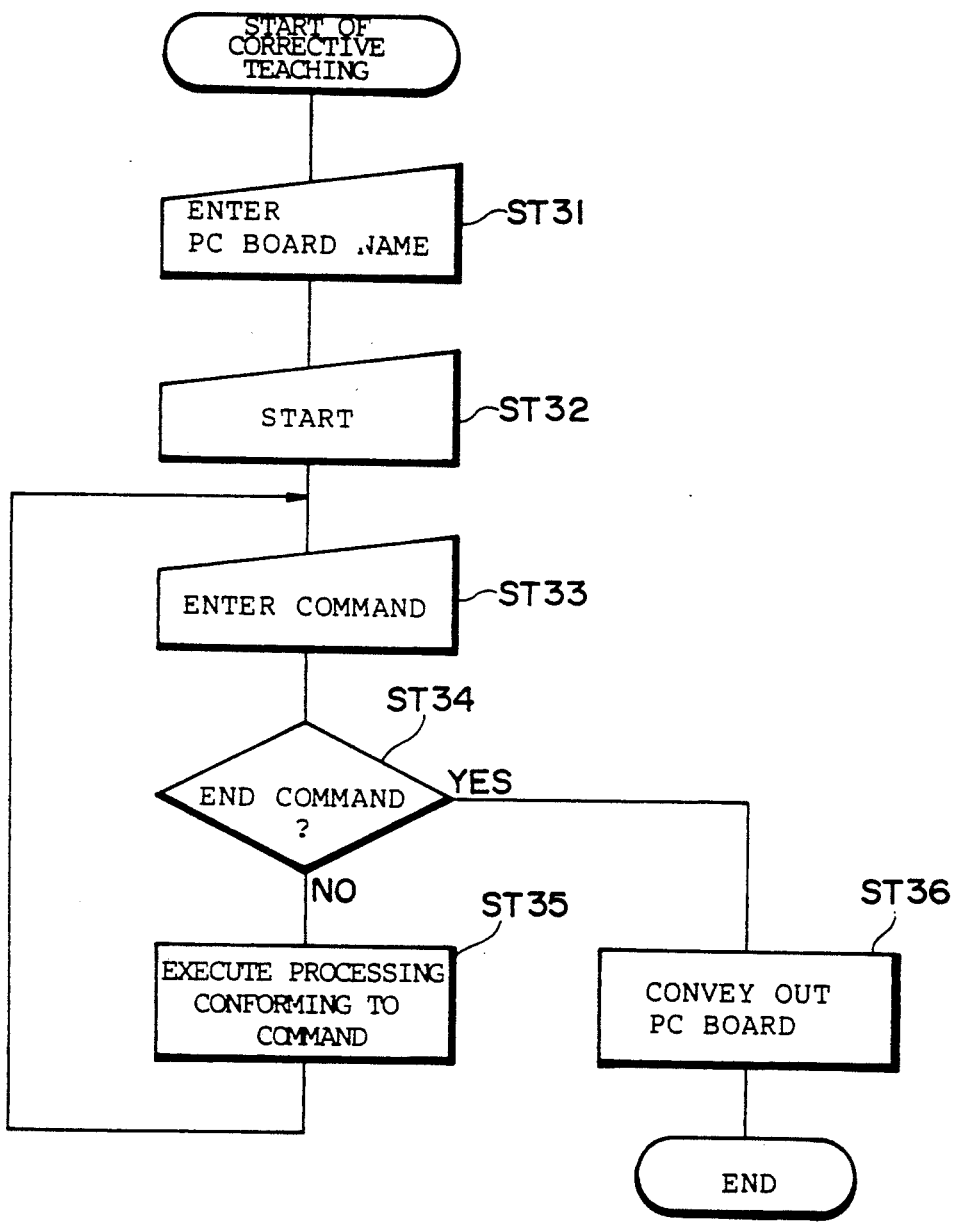
FIG. 25 is a flowchart showing a corrective teaching procedure.

When fabrication of the criteria data file ends, PC board inspection is performed using these data. In a case where an erroneous judgment is rendered in inspection of the acceptability of a soldered state, it is necessary to apply a correction to the contents taught in the above-described teaching operation. The mode for implementing this correction is referred to as corrective teaching, and the procedure thereof is illustrated in FIG. 25.

First, at step 31 the operator keys in the name of the PC board to undergo corrective teaching, then places the PC board 20T, which is to undergo inspection, on the conveyor 27 and presses the START key at step 32.

At step 33, the operator enters a command for suspending inspection, as at such time that a fault is judged to exist, and starts inspection of the PC board.

As a result, when the decision unit 36 renders a defect decision to the effect that a certain part has a soldering defect, the progress of the inspection operation is halted at step 35, and the operator manually executes the necessary processing in order to confirm whether the defect decision is erroneous and, if the decision is erroneous, to investigate the cause of the erroneous decision.

Figure 27A:
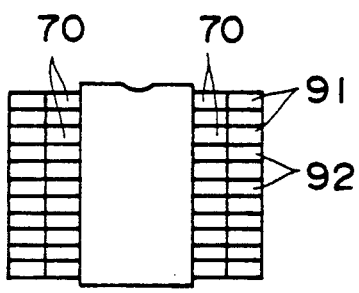
FIGS. 27a and 27b are, respectively, a view showing a display screen of a CRT display unit at the time of corrective teaching and an explanatory view showing, in enlarged form, a portion of the display screen which prevails when pattern extraction is acceptable.

More specifically, with regard to a part judged to be defective, the operator first enters a predetermined command in order to display the extracted state of each hue pattern on the CRT display unit 41 (step 33), whereupon a display of the part such as shown in FIG. 27a appears on the screen of the CRT display unit 41 (step 35).

This display includes an original image 70 of each land obtained by imaging the part mounted on the PC board 20T, an image 91 of each land, which is obtained by extracting each of the hue patterns of the three primary colors from the original image 70, and an image 92 between lands. The images 91, 92 based on the results of extraction are displayed by expressing each of the hue patterns by the pseudo color corresponding thereto. The image 92 between lands is displayed in the color black if there is no solder bridge or solder ball.

The images 91 based on the results of extraction of lands are displayed on the positions adjacent to the original image 70, that is, on the top positions of the lands, and the images 92 based on the results of extraction of the image between the lands are displayed between the images 91 adjacent to each other.

Figure 27B:
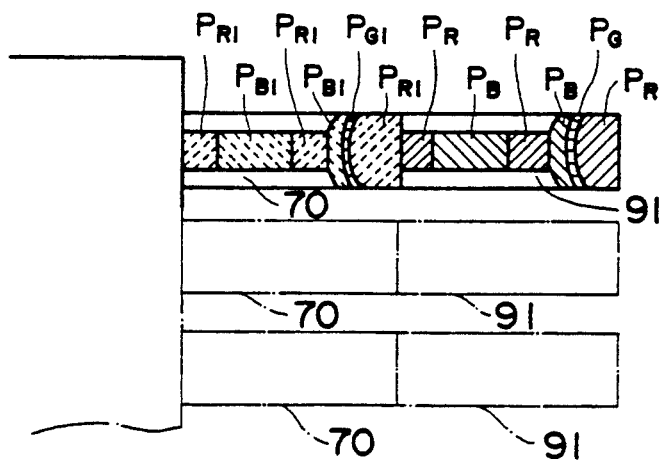

FIG. 27b illustrates, in enlarged form, the original image 70 regarding a land in a case where pattern extraction is acceptable, and the image 91 based on the results of extraction. In correspondence with a red region $p_{R1}$, green region $P_{G1}$ and blue region $p_{B1}$ of the original image 70, pattern regions $P_R$, $P_G$, $P_B$ in pseudo colors corresponding to these colors appear in the image 91 that is based on the results of extraction.

Figure 28:
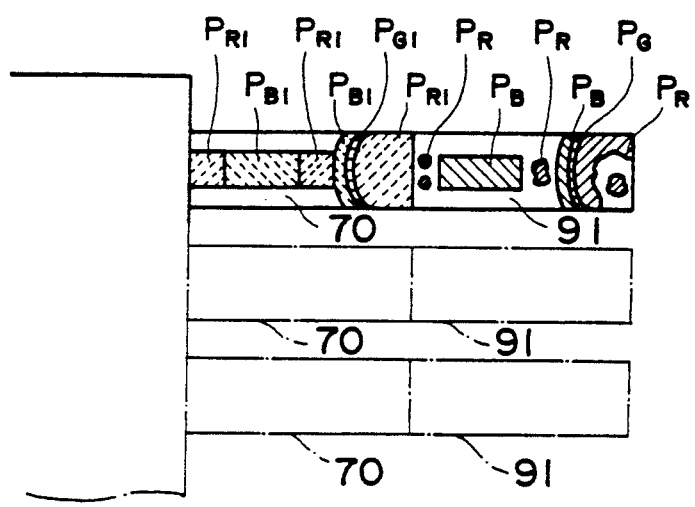
FIG. 28 is an explanatory view showing, in enlarged form, a portion of the display screen which prevails when pattern extraction is unacceptable.

FIG. 28 illustrates, in enlarged form, the original image 70 regarding a land in a case where pattern extraction is not acceptable, and the image 91 based on the results of extraction. Here the red, green and blue regions $P_{R1}$, $P_{G1}$ and $P_{B1}$ of the original image 70 and the pattern regions $P_R$, $P_G$, $P_B$ in pseudo colors of each of the hues based on the results of extraction are not in perfect correspondence. In particular, in the case of this example, the red region $P_{R1}$ and the pattern region $P_R$ based on the pseudo color of the color red do not agree. When such a display appears, it can be judged that the fixed values $T_1$, $T_2$ have been set inappropriately. These values are then set again and the images are compared in a similar manner.

When similar corrective processing is thus executed with regard to all parts for which a defect decision has been rendered and entry of an end command is confirmed at step 34, the PC board 20T is conveyed out at step 36.

When corrective teaching is completed by the foregoing operation, the PC board inspecting apparatus attains a state in which it is possible to perform an accurate, automatic inspection of the PC board 20T that is to be inspected, and a transition is made to the inspection processing shown in FIG. 8.

INDUSTRIAL APPLICABILITY

The apparatus for inspecting PC boards and the like according to the invention, and the method of operating the apparatus according to the invention, are applicable particularly to an apparatus which automatically judges the soldering acceptability of electronic parts mounted of a PC board, and the apparatus and method are useful in automating, and in reducing the labor of, a process for assembling the PC boards in electronic equipment, a process for mounting the parts of the equipment, etc.

What is claimed is:

1. An apparatus for inspecting properties of a curved surface, comprising:
   projecting means which includes three annular light sources for simultaneously generating red light, green light and blue light, respectively having light-emission energy distributions with respect to wavelength that provide white light upon being mixed, arranged at positions to project this light, at angles of incidence that differ from one another, toward a surface of a curved-surface body to be inspected;
   light-quantity adjusting means for adjusting the quantity of light of each light source in such a manner that white light is obtained when the light emitted from said light sources is mixed;
   image pickup means for imaging reflected-light images from the surface of the curved-surface body to obtain imaged patterns distinguished by hue; and
   processing means for detecting properties of a curved-surface element of the curved-surface body from the imaged patterns obtained form said image pickup means.

2. The apparatus of claim 1, where said light source comprise white-light sources covered by red, green, and blue color filters, respectively.

3. The apparatus of claim 1, where said image pickup means comprises a color television camera.

4. The apparatus of claim 1, where said processing means comprises:
   conversion means for converting said imaged patterns into digital signals, and
   image processing means for processing said digital signals and outputting an inspected data file of said imaged patterns.

5. A method for inspecting properties of a curved surface using three annular light sources which generate red light, green light, and blue light, respectively, said method comprising the steps of:
   simultaneously projecting the red light, green light, and blue light from the three annular light sources toward a surface of a curved-surface body to be inspected from different angles of incidence;
   adjusting the quantity of light from each light source in such a manner that white light is obtained when the light emitted from said light sources is mixed at the surface of the curved-surface body;
   detecting light reflected from the surface of the curved-surface body to obtain imaged patterns distinguished by hue; and
   detecting properties of a curved-surface element of the curved-surface body from the imaged patterns.

* * * * *